(12) United States Patent
Caplan et al.

(10) Patent No.: US 12,329,439 B1
(45) Date of Patent: Jun. 17, 2025

(54) ELECTRICAL ENERGY ABLATION SYSTEMS, DEVICES AND METHODS FOR THE TREATMENT OF TISSUE

(71) Applicant: Fractyl Health, Inc., Burlington, MA (US)

(72) Inventors: Jay Caplan, Boston, MA (US); Harith Rajagopalan, Wellesley Hills, MA (US); J. Christopher Flaherty, Nottingham, NH (US)

(73) Assignee: Fractyl Health, Inc., Burlington, MA (US)

( * ) Notice: Subject to any disclaimer, the term of this patent is extended or adjusted under 35 U.S.C. 154(b) by 0 days.

(21) Appl. No.: 19/046,264

(22) Filed: Feb. 5, 2025

Related U.S. Application Data

(63) Continuation of application No. 17/879,222, filed on Aug. 2, 2022, which is a continuation of application
(Continued)

(51) Int. Cl.
*A61B 18/14* (2006.01)
*A61B 17/22* (2006.01)
(Continued)

(52) U.S. Cl.
CPC .......... *A61B 18/14* (2013.01); *A61B 18/1492* (2013.01); *A61B 17/22012* (2013.01); *A61B 2018/00011* (2013.01); *A61B 2018/0016* (2013.01); *A61B 2018/00214* (2013.01); *A61B 2018/0022* (2013.01); *A61B 2018/00267* (2013.01); *A61B 2018/00285* (2013.01); *A61B 2018/00494* (2013.01); *A61B 2018/00577* (2013.01); *A61B 2018/00815* (2013.01); *A61B 2018/00821* (2013.01); *A61B 2018/00875* (2013.01); *A61B 2018/00982* (2013.01); *A61B 18/042* (2013.01); *A61B 2018/1807* (2013.01);
(Continued)

(58) Field of Classification Search
CPC . A61B 17/22012; A61B 18/042; A61B 18/14; A61B 18/1492; A61B 18/1815; A61B 18/20; A61B 2018/00011; A61B 2018/0016; A61B 2018/00214; A61B 2018/0022; A61B 2018/00267; A61B 2018/00285; A61B 2018/00494; A61B 2018/00577; A61B 2018/00815; A61B 2018/00821; A61B 2018/00875; A61B 2018/00982; A61B 2018/1807; A61B 2090/064; A61B 2090/065; A61B 90/37; A61M 13/003; A61M 2202/0225
See application file for complete search history.

(56) References Cited

U.S. PATENT DOCUMENTS

2008/0275445 A1* 11/2008 Kelly ................. A61B 18/1492
606/45

* cited by examiner

Primary Examiner — Tigist S Demie
(74) Attorney, Agent, or Firm — Wolf, Greenfield & Sacks, P.C.

(57) ABSTRACT

A device for ablating target tissue of a patient with electrical energy is provided. An elongate shaft includes a proximal portion and a distal portion, and a radially expandable element is attached to the distal portion. An ablation element for delivering electrical energy to target tissue is mounted to the radially expandable element. The device can be constructed and arranged to ablate the duodenal mucosa of a patient while avoiding damage to the duodenal adventitial tissue. Systems and methods of treating target tissue are also provided.

29 Claims, 15 Drawing Sheets

Related U.S. Application Data

No. 16/711,236, filed on Dec. 11, 2019, now Pat. No. 11,439,457, which is a continuation of application No. 14/609,332, filed on Jan. 29, 2015, now abandoned, which is a continuation of application No. PCT/US2013/052786, filed on Jul. 30, 2013.

(60) Provisional application No. 61/677,422, filed on Jul. 30, 2012.

(51) Int. Cl.
    *A61B 18/00*     (2006.01)
    *A61B 18/04*     (2006.01)
    *A61B 18/18*     (2006.01)
    *A61B 18/20*     (2006.01)
    *A61B 90/00*     (2016.01)
    *A61M 13/00*     (2006.01)

(52) U.S. Cl.
    CPC ........... *A61B 18/1815* (2013.01); *A61B 18/20* (2013.01); *A61B 2090/064* (2016.02); *A61B 2090/065* (2016.02); *A61B 90/37* (2016.02); *A61M 13/003* (2013.01); *A61M 2202/0225* (2013.01)

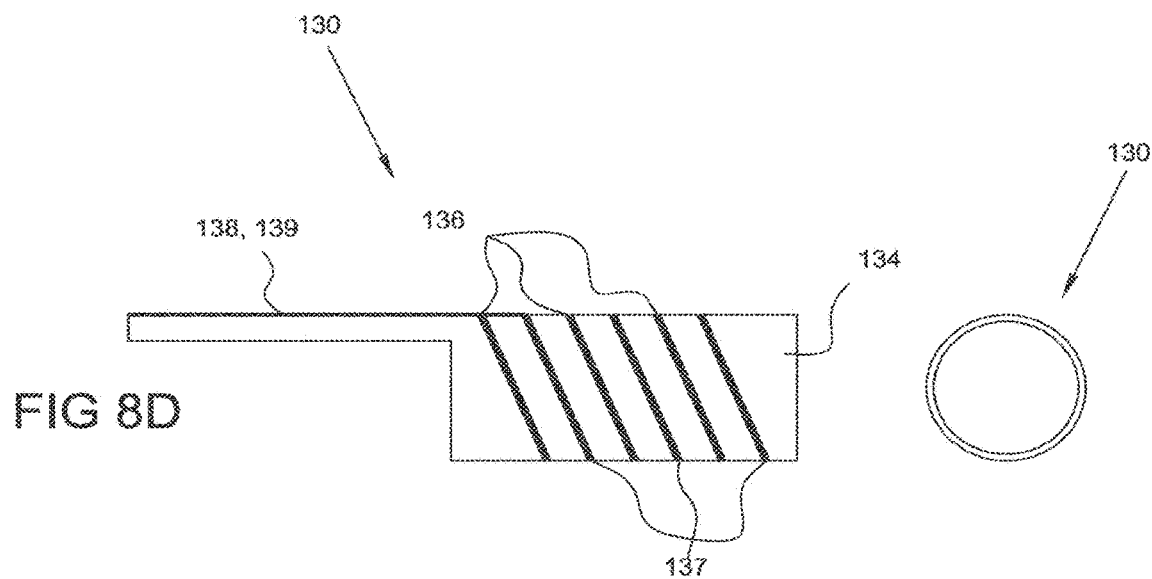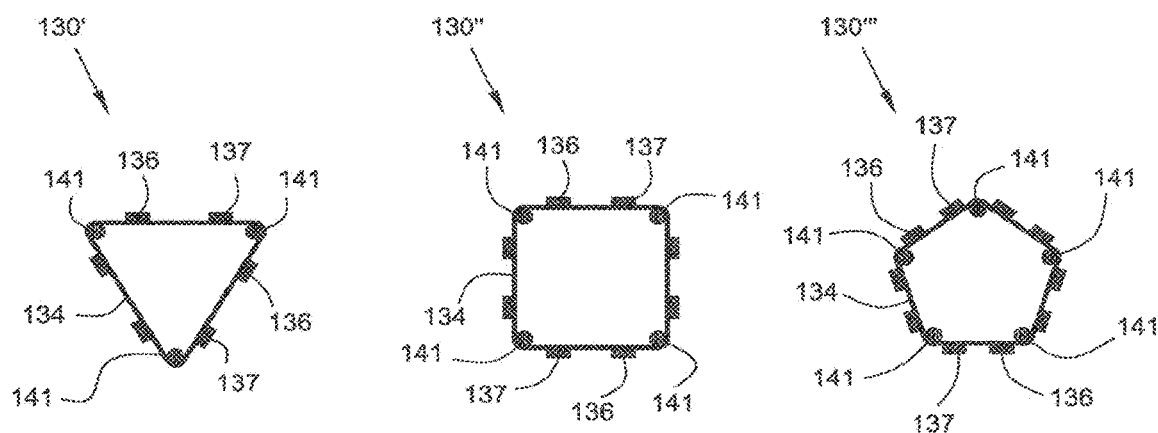

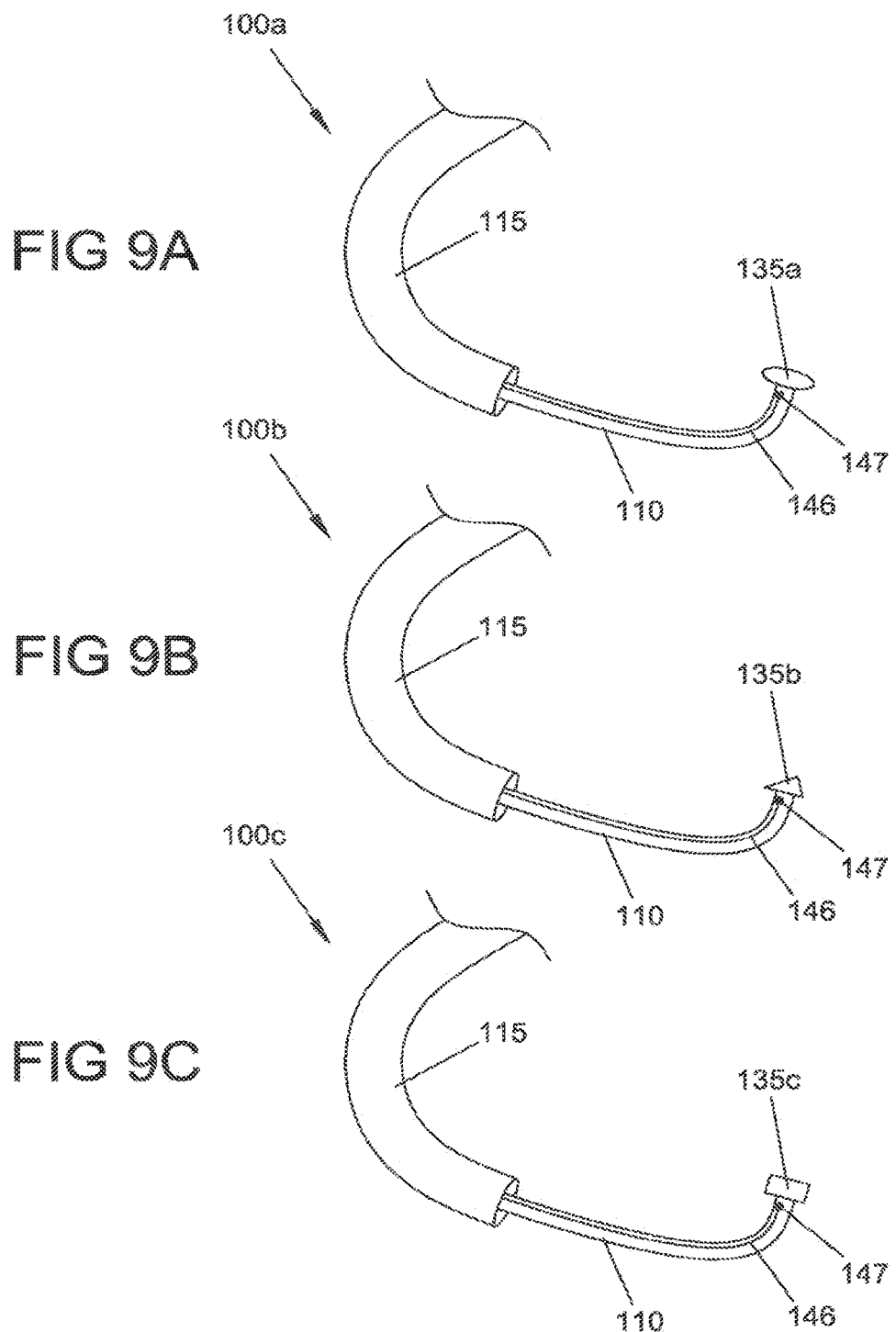

ELECTRICAL ENERGY ABLATION SYSTEMS, DEVICES AND METHODS FOR THE TREATMENT OF TISSUE

RELATED APPLICATIONS

This application is a continuation of U.S. patent application Ser. No. 17/879,222, filed Aug. 2, 2022, which is a continuation of U.S. patent application Ser. No. 16/711,236, filed Dec. 11, 2019, now U.S. Pat. No. 11,439,457, which is a continuation of U.S. patent application Ser. No. 14/609,332, filed Jan. 29, 2015, which is a continuation of International Patent Application No. PCT/US2013/052786, filed Jul. 30, 2013, which claims the benefit of U.S. Provisional Application Ser. No. 61/677,422, filed Jul. 30, 2012. Each of the above-listed applications is incorporated by reference herein in its entirety.

This application is also related to PCT Application Serial Number PCT/US2012/021739, filed Jan. 18, 2012; PCT Application Serial Number PCT/US2013/28082, filed Feb. 27, 2013; and PCT Application Serial Number PCT/US2013/37486, filed Apr. 19, 2013; the contents of each are incorporated herein by reference in their entirety.

TECHNICAL FIELD

The embodiments disclosed herein relate generally to systems, devices and methods for treating tissue, particularly gastrointestinal tissue.

BACKGROUND

Diabetes is a metabolic disease in which a person develops high blood sugar because the person's body does not produce enough insulin or the cells of the body are incapable of effectively responding to the produced insulin. Primarily, diabetes is of two types: Type-1 and Type-2. Type-1 diabetes results due to the body's failure to produce enough insulin, and Type-2 diabetes results from the body's autoimmune destruction of pancreatic beta cells and, consequently, the body's failure to produce enough insulin, and Type 2 diabetes is a complex metabolic derangement that causes hyperglycemia through insulin resistance (in which the body's cells fail to properly utilize the produced insulin) and inadequate insulin production to meet the body's needs.

Currently, there are several procedures aimed at treating diabetes based on the above concept. The procedures require major surgery, removal of portions of the gastrointestinal (GI) tract, and/or placement of one or more long-term implants. As with any major surgery, gastric bypass surgery and device implant surgery carry a risk of complications.

Devices have been developed to deliver energy to the body. For example, cardiac ablation devices have been designed to deliver ablative energy to heart tissue. Additionally, urethral resection devices have been designed to burn or cut away portions of a prostate. Each of these technologies has been modified and adapted toward effective usage in the particular portion of the body to be treated, as well as the particular disease to be treated.

There is a need for systems and methods that can provide a therapeutic treatment of the GI tract by the application of energy to the GI tract. Specifically, there is a need to provide a treatment of diabetes with a procedure in the GI tract that is less invasive than gastric bypass surgery and has other advantages for patients.

SUMMARY

According to one aspect of the present inventive concepts, a device for ablating tissue of a patient with electrical energy includes an elongate shaft with a proximal portion and a distal portion; a radially expandable element attached to the elongate shaft distal portion; and an ablation element mounted to the radially expandable element and configured to deliver electrical energy to target tissue. The device is configured to ablate mucosal tissue (e.g. duodenal mucosal tissue or other small intestine mucosal tissue) while avoiding damaging adventitial tissue or other non-target tissue. The device can be further configured to ablate at least an inner layer of duodenal submucosal tissue and/or an inner layer of other mucosal tissue of the small intestine. The device can be further configured to avoid ablating (e.g. not ablate) at least the outermost portion of submucosal tissue, such as to avoid ablating a layer comprising the outermost 100 microns, or the outermost 200 microns of duodenal submucosal tissue. The device can be further configured to ablate tissue such as: jejunal mucosal tissue; ileal mucosal tissue; and gastric mucosal tissue. The device can be further configured to minimize damage to at least one of the pylorus or the Ampulla of Vater, for example where the device includes an advanceable sheath configured to minimize damage to at least one of the pylorus or the Ampulla of Vater. The device can be further configured to identify the Ampulla of Vater. The device can include a fluid delivery element constructed and arranged to deliver fluid, gel or other material into submucosal tissue, such as to expand the submucosal tissue. The fluid delivery element can comprise multiple fluid delivery elements, such as one or more needles and/or one or more fluid jets. The device can include one or more vacuum ports positioned proximate the multiple fluid delivery elements, such as to stabilize, manipulate or otherwise apply a force to the tissue receiving the expansion material. The submucosal tissue can be expanded to increase a target treatment area. The submucosal tissue can be expanded circumferentially.

The device can be constructed and arranged to perform a target tissue treatment that modifies a tissue property selected from the group consisting of: a secretive property of a portion of the gastrointestinal tract; an absorptive property of a portion of the gastrointestinal tract; and combinations thereof.

The device can be further configured to minimize distension of duodenal tissue or other small intestine tissue. The device can be further configured to limit forces applied to a duodenal or other tissue wall, such as to limit forces to a level at or below 2.5 psi, or at or below 1 psi. The device can be further configured to apply a force of at least 0.2 psi to a tissue wall, or to apply a force of at least 0.5 psi to a tissue wall. The device can be further configured to avoid damaging tissue selected from the group consisting of: a duodenal muscularis layer; jejunal muscularis layer; ileal muscularis layer; gastric muscularis layer; Ampulla of Vater; bile duct; pancreas; pylorus; muscularis externae; serosa; and combinations of these. The device can be further configured to ablate mucosal tissue in a curved segment of the small intestine, such as a curved segment of the duodenum. The device can be further configured to ablate a tissue layer of at least 500 microns. The device can be further configured to ablate a volume of tissue having a surface area and a depth, where the depth is less than approximately 1.0% its surface area, or less than approximately 0.1% its surface area.

The elongate shaft of the device can be configured to be passed through the working channel of an endoscope. The shaft can have a diameter of less than or equal to 6 mm, or less than or equal to 4.2 mm, or less than or equal to 3.8 mm, or less than or equal to 3.2 mm, or less than or equal to 2.8 mm. The elongate shaft can be configured to pass alongside an endoscope that has been placed in a gastrointestinal tract. The device can be configured for over-the-wire delivery, such as over-the-wire delivery through the gastrointestinal tract.

The device can be configured to treat substantially the entire length of the target tissue simultaneously, such as to treat the entire length of the duodenum simultaneously. The device can be configured to treat a first length of small intestine (e.g. a first length of duodenum) in a first energy application and a second length of small intestine (e.g. a second length of duodenum) in a second energy application. In some embodiments, the first length of duodenum or other length of small intestine overlaps the second length of duodenum or other length of small intestine. In some embodiments, the first length of duodenum or other length of small intestine includes a first central axis and the second length of duodenum or other length of small intestine includes a second central axis non-parallel with the first axis. The device can be configured to treat at least three lengths of small intestine with at least three energy treatments, such as where the at least three lengths of small intestine comprise at least 50% of the length of the duodenum. The device can be configured to deliver the electrical energy based on a measured diameter of the small intestine, for example where the measured diameter is measured by at least one radially expandable element of the device and/or by one or more radially expandable elements of a separate device.

The device radially expandable element can have a length less than or equal to approximately 20 mm. The radially expandable element can be configured to be relatively rigid during the delivery of the electrical energy to the target tissue, for example where the ablation element includes multiple parallel conductors, and where the relatively rigid radially expandable element is configured to maintain spacing between the multiple parallel conductors. The radially expandable element can include at least a portion that is round when expanded. The radially expandable element can include at least a portion that, when expanded, includes a tissue-contacting shape selected from the group consisting of: triangle; rectangle; pentagon; hexagon; trapezoid; and combinations of these. The tissue-contacting shape can be selected to allow an operator to treat one or more target tissue portions without leaving gaps and/or to limit the number of repeated ablations needed to cover a target tissue portion regularly or irregularly shaped area. The radially expandable element can be configured to be folded to a radially compacted state from its radially expanded state. The radially expandable element can be configured to linearize curvilinear gastrointestinal tissue. The radially expandable element can be configured to distend gastrointestinal tissue.

In some embodiments, the radially expandable element includes a balloon, for example a compliant balloon, a non-compliant balloon, and/or a pressure-threshold balloon. The balloon can include an external surface and the ablation element can be mounted to the balloon external surface. The radially expandable element can further include a scaffold biased in a radially expandable condition. The device can further include at least one inflation lumen in fluid communication with the balloon.

In some embodiments, the radially expandable element includes a radially expandable scaffold. Examples of radially expandable scaffolds include: an expandable cage; a stent-like structure; an array of splines; and combinations of these. The radially expandable scaffold can include multiple filaments configured to expand to a diameter of at least 20 mm, or at least 25 mm, or at least 30 mm, where the device includes a distal portion configured to be slidingly received by a channel with a diameter less than or equal to 6 mm. The radially expandable scaffold can include a scaffold resiliently biased in a radially expanded condition. The device can further include a control shaft configured to expand the radially expandable scaffold when retracted. The radially expandable scaffold can include an array of splines, for example where the ablation element includes at least a first electrode mounted to a first spline and a second electrode mounted to the first spline. Alternatively, the ablation element includes at least a first electrode mounted to a first spline and a second electrode mounted to a second spline. The radially expandable scaffold can include an oval or football shaped scaffold, or a relatively unidiameter scaffold.

In some embodiments, the radially expandable element includes multiple radially deployable arms.

In some embodiments, the radially expandable element includes a radially expandable tube. For example, the radially expandable tube can include a tube resiliently biased in an expanded condition.

In some embodiments, the radially expandable element includes a radially expandable sheet. The radially expandable sheet can include a sheet resiliently biased in an expanded condition, for example where the radially expandable sheet is configured to be furled to transition to a compact condition. The radially expandable sheet can include a sheet resiliently biased in an unexpanded condition, for example where the radially expandable sheet is configured to be unfurled to transition to an expanded condition. The radially expandable sheet can include a foldable sheet, for example a sheet configured to be folded to transition from an expanded state to an unexpanded state and configured to be unfolded to transition from an unexpanded state to an expanded state.

The radially expandable element can have a diameter ranging from 15 mm to 30 mm. The radially expandable element can have a length ranging from 10 mm to 40 mm, such as a length ranging from 20 mm to 25 mm, or a length of less than or equal to 15 mm. In some embodiments, the radially expandable element can include at least two radially expandable elements each with a length less than or equal to 25 mm, for example less than 20 mm.

The radially expandable element can be configured to be moved in a motion selected from the group consisting of: rotation; translation; and combinations thereof. In some embodiments, the radially expandable element can be moved manually, for example by an operator. In some embodiments, the device can include a motion transfer assembly configured to move the radially expandable element. In some embodiments, the ablation element can be configured to deliver a first energy delivery and a second energy delivery, and the radially expandable element can be configured to be moved between the first energy delivery and the second energy delivery. In some embodiments, the ablation element is configured to be moved during the delivery of the electrical energy.

In some embodiments, the radially expandable element includes an expandable helical structure. The radially expandable element can further include a filament comprising the ablation element and can be configured to be moved along the helical structure, for example where a motion transfer assembly moves the filament during the delivery of electrical energy.

The device can further include a second radially expandable element. In some embodiments, the second radially expandable element can be configured to perform a luminal diameter measurement. In some embodiments, the second radially expandable element includes a second ablation element configured to deliver electrical energy to target tissue. In this embodiment, the first radially expandable element has a first length, and the first radially expandable element and the second radially expandable element are spaced apart by a distance less than or equal to the first length, for example where the second radially expandable element has a second length approximately the same as the first radially expandable element length. In some embodiments, the first radially expandable element has a length of less than or equal to approximately 20 mm and the second radially expandable element has a length of less than or equal to approximately 20 mm. The device can further include multiple filaments extending between the first radially expandable element and the second radially expandable element. In some embodiments, the multiple filaments include multiple elongate conductors and the multiple elongate conductors include the ablation element. In some embodiments, the ablation element includes multiple electrodes mounted to the multiple filaments. In some embodiments, the ablation element includes a first set of electrodes positioned on the first radially expandable element and a second set of electrodes positioned on the second radially expandable element, for example where the first set of electrodes are configured in a first geometry and the second set of electrodes are configured in a second geometry different than the first, such as where the first geometry and second geometry are configured such that ablation with the first geometry and the second geometry causes substantially full surface ablation of an area of tissue. In some embodiments, the second radially expandable element is positioned within the first radially expandable element, for example where the ablation element includes a first set of electrodes positioned on the first radially expandable element and a second set of electrodes positioned on the second radially expandable element. In some embodiments, the first radially expandable element is positioned within the second radially expandable element, and the second radially expandable element includes insulating material and a set of openings, for example where the insulating material includes an inflatable balloon. In this embodiment, the ablation element can include a top surface area where each opening of the set of openings includes an opening area less than an electrode top surface area.

The device can further include a second radially expandable element distal to the first radially expandable element and a third radially expandable element distal to the second radially expandable element, where the second radially expandable element includes a second ablation element and the third radially expandable element includes a third ablation element. In some embodiments, the first radially expandable element, the second radially expandable element and the third radially expandable element each includes a length of less than or equal to approximately 20 mm. In some embodiments, the first and second ablation elements are separated by a first distance and the second and third ablation elements are separated by a second distance similar to the first distance. In some embodiments, the target tissue includes a set of sequential target tissue portions comprising, in order, a first section, a second section, a third section, a fourth section, and a fifth section, and wherein the first, second and third ablation elements are configured to ablate the first, third and fifth target tissue portions in a first energy delivery and the first and second ablation elements are configured to ablate the second and fourth target tissue portions in a second energy delivery.

The radially expandable element can be configured to be radially compacted to stop the delivery of the electrical energy.

The device can further include a control shaft operably coupled to the radially expandable element, where translation of the control shaft changes the shape of the radially expandable element. For example, retraction of the control shaft causes the radially expandable element to expand and advancement of the control shaft causes the radially expandable element to expand.

The ablation element can be configured to cause non-desiccating ablation of the target tissue. The ablation element can be configured to minimize electrical current driven temperature increase in the outermost 50% of the mucosal layer, for example where the outermost 50% of the mucosal layer is ablated mainly due to thermal conduction. The ablation element can be configured to minimize electrical current driven temperature increase in the outermost 80% of the mucosal layer, for example where the outermost 80% of the mucosal layer is ablated mainly due to thermal conduction.

In some embodiments, at least a portion of the ablation element includes a surface area with a geometric shape comprising: a linear segment; a circle; a rectangle; and combinations of these.

In some embodiments, the ablation element includes at least a single pair of electrodes. The single pair of electrodes can include a first electrode comprising multiple elongate conductors and a second electrode comprising multiple elongate conductors. For example, the first electrode can include a first elongate conductor comprising a major axis that is configured to be relatively parallel to a central axis of a portion of the small intestine (e.g. duodenum) during delivery of energy where the first elongate conductor major axis that is configured to be relatively parallel to a central axis of a curvilinear portion of the small intestine (e.g. duodenum) during energy delivery. The first elongate conductor major axis can be configured to be relatively parallel to a central axis of a curvilinear portion of the small intestine during energy delivery. The first electrode multiple elongate conductors can include conductors with a length of at least 10 mm, for example at least 20 mm. The first electrode multiple elongate conductors and the second electrode multiple elongate conductors can be positioned in an interdigitated array, for example where the interdigitated conductors are edge-to-edge spaced at a distance less than or equal to 1.5 mm, for example less than or equal to 1.0 mm or less than or equal to 750 microns. The first electrode multiple elongate conductors and the second elongate multiple elongate conductors can be positioned relatively parallel to each other. The first electrode multiple conductors can include at least 4 elongate conductors.

In some embodiments, the ablation element includes at least one pair of electrodes. The ablation element can be configured to deliver a current, where the current passes substantially through the innermost 50% of the mucosal layer, or through the innermost 20% of the mucosal layer.

In some embodiments, the ablation element includes at least one conductor comprising a height that extends from the radially expandable element at least 100 microns. The at least one conductor can include a tissue contacting surface positioned at least 200 microns from the surface of the radially expandable element, for example where the at least one conductor tissue contacting surface is positioned at least 400 microns from the radially expandable element. The at least one conductor can include an electrically insulating material between the tissue contacting surface and the radially expandable element, for example where the electrically insulating material includes polytetrafluoroethylene.

In some embodiments, the ablation element includes at least 2 electrodes. In some embodiments, the ablation element includes at least 4 electrodes.

In some embodiments, the ablation element includes at least one conductor with a length of approximately between 10 mm and 40 mm.

In some embodiments, the ablation element includes a first conductor and a second conductor with an edge-to-edge spacing between approximately 200 microns and 2 mm.

In some embodiments, the ablation element includes at least one conductor with a width less than or equal to 2.0 mm, for example a width less than or equal to 1.5 mm or a width less than or equal to 1.0 mm, or a width between 400 microns and 700 microns.

In some embodiments, the ablation element includes at least one conductor with a width greater than 230 microns.

In some embodiments, the ablation element includes at least two conductors with a width of approximately 400 microns, for example where the at least two conductors with an edge to edge spacing of approximately 600 microns.

In some embodiments, the ablation element includes at least one conductor with a width of approximately 700 microns, for example where the at least two conductors with an edge to edge spacing of approximately 400 microns.

In some embodiments, the ablation element includes at least one conductor with a width less than or equal to a desired depth of ablation. In some embodiments, the ablation element includes a first conductor and a second conductor separated by a first distance, where the first distance is less than or equal to a desired depth of ablation. In some embodiments, the ablation element includes an array of conductors. For example, the array of conductors can include a circumferential array of conductors such a linear or curvilinear circumferential array of conductors. In some embodiments, the circumferential array of conductors comprises a helical array of conductors. In some embodiments, the circumferential array of conductors includes a 360° array. In some embodiments, the circumferential array of conductors is configured to prevent formation of a full circumferential scar, for example where the array of conductors includes a less than 350° array of conductors such as a 300° to 350° array of conductors. In some embodiments, the circumferential array of conductors includes an array of conductors spanning approximately 45° to 300°, for example where the device is configured to be rotated to treat a 360° segment of target tissue. In some embodiments, the circumferential array of conductors includes multiple pairs of conductors, for example at least five pairs of conductors. In some embodiments, the circumferential array of conductors includes conductors radially edge-to-edge spaced at a distance between approximately 230 microns and 2.0 mm, for example at a distance between approximately 400 microns to 600 microns. In some embodiments, the circumferential array of conductors includes conductors radially spaced at a first distance, where the width of the multiple conductors is approximately half of the first distance. In some embodiments, the circumferential array of conductors includes conductors radially spaced with a uniformity of spacing greater than or equal to 95%, for example with a uniformity of spacing greater than or equal to 98%.

In some embodiments, the ablation element includes an elongate copper conductor.

In some embodiments, the ablation element includes a shape selected from the group consisting of: a rectangle; a square; a triangle; a trapezoid; and combinations of these.

The ablation element can be configured to ablate tissue in a shape selected from the group consisting of: a rectangle; a square; a triangle; a trapezoid; and combinations thereof.

In some embodiments, the ablation element includes multiple conductors arranged in an operator adjustable pattern. In some embodiments, the ablation element includes multiple flexible conductors.

In some embodiments, the ablation element is mounted to the radially expandable element by at least one of: a glue joint; a weld; a swage or a molecular bond. In some embodiments, the ablation element is at least partially embedded in the radially expandable element.

The device can further include a flexible substrate, where the ablation element is attached to the flexible substrate. The flexible substrate can include a material selected from the group consisting of: polyamide; a polyester weave; a stretchable polyurethane material; and combinations of these. The flexible substrate can include a heat set configured to enhance folding of the flexible substrate. The ablation element can include multiple conductors deposited on the flexible substrate, for example where the ablation element includes at least one conductor deposited using an ink-jet deposition process, such as where the at least one conductor is deposited by depositing catalytic ink followed by exposure to a copper solution. The ablation element can include at least one conductor deposited using a masked deposition process. The radially expandable element can include at least three splines, where the substrate is attached to the at least three splines. The at least three splines can be arranged in a symmetric circumferential pattern. The at least three splines can form a non-circular cross section when the radially expandable element is expanded. The expandable element can include four splines such that when the expandable element is expanded, the substrate includes a relatively square cross section. The expandable element can include five splines such that when the expandable element is expanded, the substrate includes a relatively pentagonal cross section or a relatively hexagonal cross section.

In some embodiments, the ablation element includes multiple wires.

In some embodiments, the ablation element includes multiple conductors configured to rotate, for example where the multiple conductors are configured to rotate during the delivery of the electrical energy.

In some embodiments, the ablation element includes an anti-stick coating, for example a polytetrafluorocthylene coating.

In some embodiments, the ablation element includes at least one conductor configured to capacitively couple the electrical energy to the target tissue. The device can be configured to position the at least one conductor such that a gap is present between the ablation element and the target tissue. The device can further include a dielectric covering positioned between the at least one conductor and the target tissue, for example where the dielectric covering comprises polytetrafluoroethylene. The dielectric covering can include a non-uniform thickness covering including dielectric material, for example where the dielectric covering includes a middle portion with a first thickness and an edge portion with a second thickness greater than the first thickness. The non-inform thickness covering can be configured to cause uniform ablation depth of a tissue area.

In some embodiments, the ablation element includes multiple conductors and the device further includes multiple insulators positioned between the multiple conductors. The multiple insulators can include multiple thermal conductors.

Examples of insulator materials include: sapphire; fused quartz; fused silica; a polymeric material; glass; and combinations of these.

The device can further include a second ablation element. The second ablation element can include an ablation element selected from the group consisting of: an RF energy delivery element such as one or more electrodes, each comprising one or more elongate conductors; an ultrasonic transducer such as one or more piezo crystals configured to ablate tissue; a laser energy delivery element such as one or more optical fibers and/or laser diodes; a heat delivery element such as a hot fluid filled balloon; a rotating ablation element; a circumferential array of ablation elements; and combinations of these.

The electrical energy delivered by the ablation element can include bipolar radiofrequency energy and/or monopolar radiofrequency energy.

In some embodiments, the elongate shaft distal portion is configured to be at least one of deflected or steered.

The device can further include at least one sensor configured to provide a signal. The device can be configured to deliver the electrical energy based on the at least one sensor signal. Examples of sensors include but are not limited to: temperature sensor; pressure sensor; impedance sensor; visual sensor; and combinations of these. The visual sensor can be configured to provide an image of tissue, for example where the visual sensor includes an imaging device selected from the group consisting of: visible light camera; infrared camera; CT Scanner; MRI; and combinations of these. The device can be configured to deliver the electrical energy based on the visual sensor signal, for example where the device is configured to deliver the electrical energy based on a change in tissue color. The at least one sensor can include multiple temperature sensors, for example multiple temperature sensors positioned with a spacing of at least 1 sensor per 1 $cm^2$. The ablation element can be configured to deliver the electrical energy based on one or more signals from the multiple temperature sensors. Examples of temperature sensors include but are not limited to: thermocouple; thermistor; resistance temperature detector; optical temperature sensor; and combinations of these. The at least one sensor can include a sensor configured to assess apposition of a device component with a gastrointestinal wall, for example where the at least one sensor includes a sensor configured to assess apposition of a balloon expanded to contact the gastrointestinal wall. The at least one sensor can include a chemical sensor, for example a carbon dioxide sensor. The at least one sensor can be configured to assess the apposition of the radially expandable element. The device can further include a second radially expandable element, where the at least one sensor is configured to assess the apposition of the second radially expandable element.

The device can further include a conductive gel configured to be applied to the target tissue, for example a gel that is at least thermally or electrically conductive. The thermally conductive gel can be configured to conduct heat into tissue. Alternatively or additionally, the thermally conductive gel can be configured to cool tissue, for example when cool air is delivered to at least one of the gel or the tissue. The electrically conductive gel can be configured to improve transfer of electrical energy to tissue. The conductive gel can be placed on tissue and/or the ablation element prior to expansion of the radially expandable element.

The device can further include an impedance monitoring assembly configured to measure impedance of tissue, for example where the device is configured to deliver the electrical energy to the target tissue based on the measured impedance.

According to another aspect of the present inventive concepts, a system for ablating tissue with electrical energy includes an ablation device, for example an ablation device as has been described hereabove, and an energy delivery unit configured to delivery electrical energy to the ablation element of the ablation device. The system can include a fluid delivery element constructed and arranged to deliver fluid, gel or other material into submucosal tissue, such as to expand the submucosal tissue. The fluid delivery element can comprise multiple fluid delivery elements, such as one or more needles and/or one or more fluid jets. The system can include one or more vacuum ports positioned proximate the multiple fluid delivery elements, such as to stabilize, manipulate or otherwise apply a force to the tissue receiving the expansion material. The submucosal tissue can be expanded to increase a target treatment area. The submucosal tissue can be expanded circumferentially.

The system can be configured to treat mucosal tissue of the small intestine, such as duodenal mucosal tissue.

The system can be constructed and arranged to perform a target tissue treatment that modifies a tissue property selected from the group consisting of: a secretive property of a portion of the gastrointestinal tract; an absorptive property of a portion of the gastrointestinal tract; and combinations thereof. The system can include at least one fluid delivery device constructed and arranged to deliver fluid into submucosal tissue to increase the volume of the target tissue.

The system delivery unit can be configured to perform a non-desiccating ablation of the target tissue.

The system can be configured to deliver energy to the target tissue with an average power density less than or equal to 20 Watts per $cm^2$, for example an average power density less than or equal to 10 Watts per $cm^2$ or an average power density less than or equal to 4 Watts per $cm^2$. The system can be configured to deliver energy to a portion of the target tissue for at least 1 second, or for at least 5 seconds, or for at least 10 seconds, or for at least 20 seconds. The system can be configured to deliver energy to the target tissue at a level that decreases over time.

The system can be configured to modulate the energy delivered to the target tissue. For example, the system can be configured to pulse-width modulate the energy delivered to the target tissue where the pulse-width modulation comprises a cycle time, an on-time and an off-time, where the on-time is no more than 20% of the cycle time. The energy delivery unit can include an electrical energy source less than or equal to a 300 Watt source, for example an electrical energy source less than or equal to a 150 Watt source.

The system can be configured to increase the temperature of the target tissue rapidly during energy delivery to the target tissue, for example at a rate of at least 17.5° C. per second. The system can be configured to increase the temperature of the target tissue to a setpoint, where the setpoint temperature ranges between 60° C. and 90° C., for example between 65° C. and 80° C.

The system can be configured to deliver electrical energy to a setpoint temperature, and maintain the tissue at the setpoint temperature for approximately 2 to 40 seconds. The setpoint temperature can range between 60° C. and 90° C., for example between 75° C. and 85° C., and the tissue can be maintained at the setpoint temperature for approximately 15 to 25 seconds.

The system can be configured to deliver electrical energy to a setpoint temperature, where one or more energy delivery parameters decay after the setpoint temperature is achieved. For example, the one or more energy delivery parameters decay at a rate configured to match a physiological response of the tissue receiving the electrical energy.

The energy delivery unit can be configured to deliver radiofrequency energy to the ablation element of the ablation device, for example radiofrequency energy at a frequency at or below 1 MHZ.

The electrical energy delivered by the ablation element can include monopolar and/or bipolar radiofrequency energy.

The electrical energy delivered by the ablation element can include a power of less than or equal to 300 W, such as a power of approximately 260 W. In one example, the power decreases from 260 W to 0W over approximately 30 seconds.

The energy delivery unit can deliver electrical energy to the ablation element in a current-driven mode.

The system can be configured to deliver electrical energy to tissue and avoid desiccation of the tissue. The system can be configured to deliver electrical energy to tissue and avoid creation of steam. The system can be configured to deliver electrical energy to tissue and avoid detachment of tissue particles. The system can be configured to deliver energy in at least 2 second energy delivery durations, for example where the at least 2 second energy delivery durations are non-continuous.

The system can further include a second ablation device for ablating luminal wall tissue. In some embodiments, the second ablation device is similar to the first ablation device of the system described hereabove. In some embodiments, the second ablation device includes a radially expandable element with a different expanded diameter than the first ablation device radially expandable element. In some embodiments, the first ablation device ablation element includes a first set of multiple conductors, and the second ablation device includes a second ablation element comprising a second set of multiple conductors, where the first set of multiple conductors are arranged in a different pattern than the second set of multiple conductors. The second ablation device can include an ablation device selected from the group consisting of: hot fluid filled balloon device; vapor ablation device; cryoablation device; laser ablation device; ultrasound ablation device; and combinations of these.

The system can further include a cooled fluid delivery device configured to deliver fluid below 37° C. to target tissue. The cooled fluid can include a liquid; a gas; and combinations of these. The cooled fluid delivery device can be configured to deliver a cooled gas toward the wall of the small intestine (e.g. duodenal wall). The cooled fluid can be delivery prior to and/or after the delivery of the electrical energy.

The system can further include an endoscope.

The system can further include a tissue expansion device, for example where the tissue expansion device includes a submucosal tissue expansion device configured to expand small intestine submucosal tissue (e.g. duodenal submucosal) tissue prior to the ablation element of the ablation device delivering the electrical energy. The tissue expansion device can comprise one or more fluid delivery elements, such as one or more needles and/or one or more water jets. The one or more fluid delivery elements can be arranged in a linear or circumferential array. The tissue expansion device can be constructed and arranged to perform a circumferential or near circumferential expansion of tubular tissue, such as a circumferential expansion of submucosal tissue of a segment of the duodenum or other small intestine segment.

The system can further include an insufflation device. In some embodiments, the system further includes an endoscope having a fluid delivery tube where the fluid delivery tube includes and/or is otherwise configured as an insufflation device. The system can be configured to control apposition of the ablation element with target tissue.

The system can further include a tissue cooling device. The tissue cooling device can be configured to apply cooling fluid to tissue, for example prior and/or after the delivery of electrical energy to the tissue. The tissue cooling device can be configured to deliver a tissue cooling gas. Examples of tissue cooling gas include: air; carbon dioxide; nitrogen; nitrous oxide; and combinations of these. The system can further include a drying assembly configured to remove moisture from the cooling gas prior to delivery. The tissue cooling device can provide cooling fluid at a temperature less than or equal to 20° C., or example a cooling fluid at a temperature less than or equal to 0° C.

According to another aspect of the present inventive concepts, a device for ablating tissue of a patient with electrical energy comprises an elongate shaft, a radially expandable element and an ablation element. The elongate shaft has a proximal portion and a distal portion. The radially expandable element is attached to the elongate shaft distal portion. The ablation element is mounted to the radially expandable element. The ablation element is constructed and arranged to deliver electrical energy to target tissue. The device is constructed and arranged to modify a tissue property selected from the group consisting of: a secretive property of a portion of the gastrointestinal tract; an absorptive property of a portion of the gastrointestinal tract; and combinations thereof. The device can further comprise at least one fluid delivery element constructed and arranged to deliver fluid into submucosal tissue to increase the volume of the target tissue. The device can be constructed and arranged as described hereabove.

BRIEF DESCRIPTION OF THE DRAWINGS

The advantages of the technology described above, together with further advantages, may be better understood by referring to the following description taken in conjunction with the accompanying drawings. The drawings are not necessarily to scale, emphasis instead generally being placed upon illustrating the principles of the technology.

FIG. 8D is side and end views of an expandable assembly including a helical array of conductors, consistent with the present inventive concepts.

FIG. 8E is an end view of an expandable assembly comprising three splines and a surrounding substrate including multiple electrodes and expanded to a triangular cross section, consistent with the present inventive concepts.

FIG. 8F is an end view of an expandable assembly comprising four splines and a surrounding substrate including multiple electrodes and expanded to a square cross section, consistent with the present inventive concepts.

FIG. 8G is an end view of an expandable assembly comprising five splines and a surrounding substrate including multiple electrodes and expanded to a pentagonal cross section, consistent with the present inventive concepts.

FIGS. 9A, 9B and 9C are distal portions of three ablation devices with three different tissue contacting portions, consistent with the present inventive concepts.

DETAILED DESCRIPTION OF THE DRAWINGS

Figure 1:
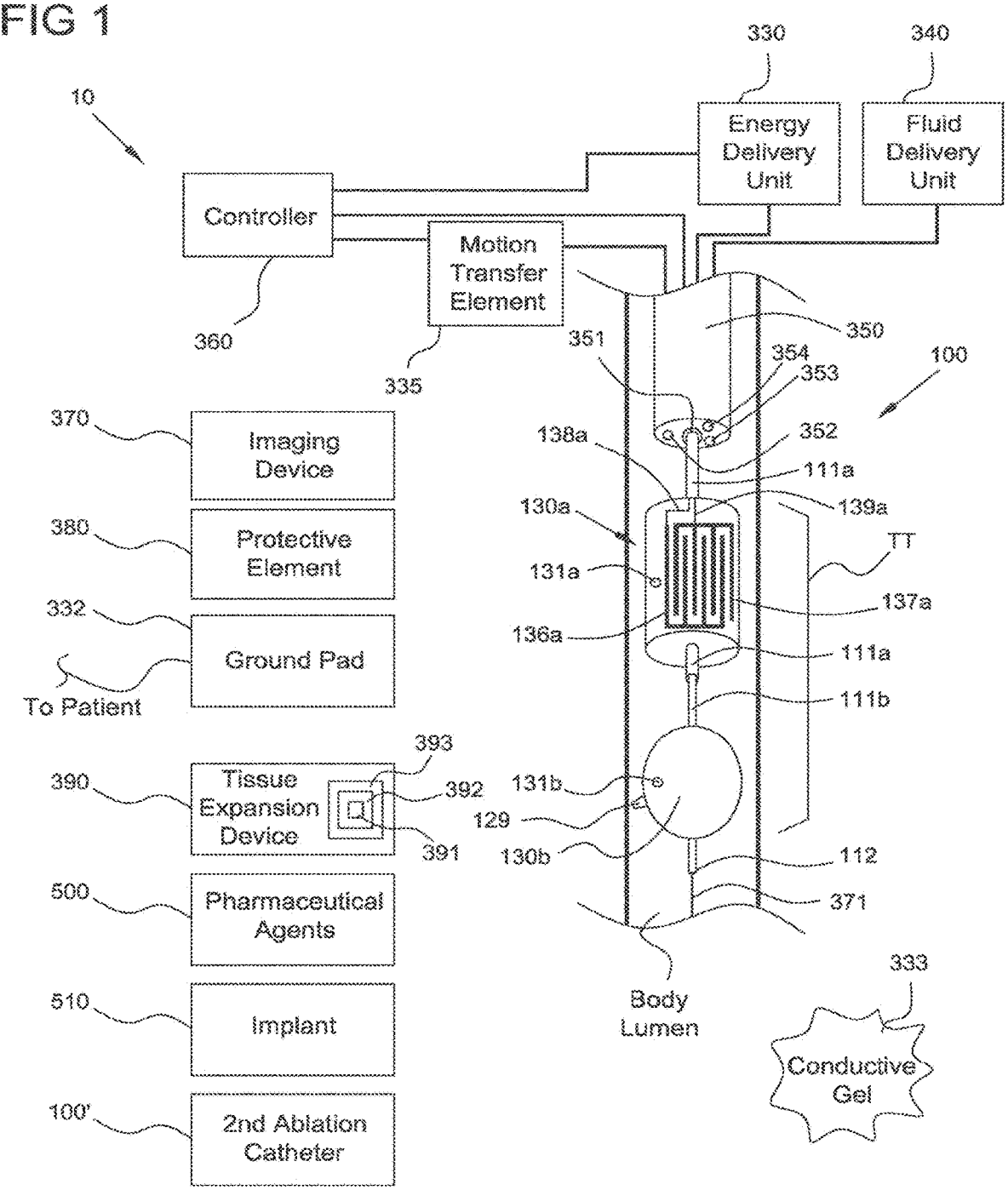
FIG. 1 is a system for ablating or otherwise treating target tissue, consistent with the present inventive concepts.

Reference will now be made in detail to the present embodiments of the inventive concepts, examples of which are illustrated in the accompanying drawings. Wherever practical, the same reference numbers will be used throughout the drawings to refer to the same or like parts.

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

It is an object of the present inventive concepts to provide systems, methods and devices for safely and effectively ablating a volume of tissue (the "target tissue"), such as one or more layers of a portion of tubular or solid tissue, such as tissue of an organ or tissue of the gastrointestinal tract of a patient. The systems and device of the present inventive concepts include one or more treatment assemblies configured to treat the target tissue, such as an assembly comprising a radially expandable element configured to be expanded and one or more ablation elements configured to deliver energy such as electrical energy to the target tissue. In some embodiments, the treatment elements are constructed and arranged as described in applicant's co-pending International PCT Application Serial Number PCT/US12/21739, entitled "Devices and Methods for the Treatment of Tissue", filed Jan. 18, 2012, the contents of which is incorporated herein by reference in its entirety.

A treatment assembly can be configured to treat target tissue in one or more locations of the patient, such as one or more contiguous or discontiguous tissue locations. The target tissue comprises a three dimensional volume of tissue, and can include a first portion, a treatment portion, whose treatment has a therapeutic benefit to a patient; as well as a second portion, a "safety-margin" portion, whose treatment has minimal or no adverse effects to the patient. Non-target tissue can be identified (e.g. prior to and/or during the medical procedure), wherein the non-target tissue comprises tissue whose treatment by the treatment assembly should be reduced or avoided such as to reduce or prevent an undesired effect.

The target tissue treatment can cause one or more effects to the target tissue such as an effect selected from the group consisting of: modification of cellular function; cell death; apoptosis; instant cell death; cell necrosis; denaturing of cells; removal of cells; and combinations of these. In some embodiments, the target tissue treatment is constructed and arranged to create scar tissue. Target tissue can be selected such that after treatment the treated target tissue and/or tissue that replaces the target tissue functions differently than the pre-treated target tissue, such as to have a therapeutic benefit. The modified and/or replacement tissue can have different secretions and/or quantities of secretions than the pre-treated target tissue, such as to treat diabetes and/or obesity. The modified and/or replacement tissue can have different absorptive properties than the target tissue, such as to treat diabetes, obesity and/or hypercholesterolemia. The effect of the treatment can occur acutely, such as within twenty four hours, or after longer periods of time such as greater than twenty four hours or greater than one week.

Target tissue to be treated can comprise two or more tissue portions, such as a first tissue portion treated with a first treatment and/or a first treatment assembly, and a second tissue portion treated with a second treatment and/or a second treatment assembly. The first and second tissue portions can be adjacent and they can contain overlapping portions of tissue. The first and second treatment and/or treatment assemblies can be similar or dissimilar. Dissimilarities can include type and/or amount of energy to be delivered by an energy delivery based treatment assembly. Other dissimilarities can include but are not limited to: target tissue area treated; target tissue volume treated; target tissue length treated; target tissue depth treated; target tissue circumferential portion treated; energy delivery type; energy delivery rate and/or amount; peak energy delivered; average temperature of target tissue treatment; maximum temperature achieved during target tissue treatment; temperature profile of target tissue treatment; duration of target tissue treatment; and combinations of these.

Target tissue can include tissue of the duodenum, such as tissue including all or a portion of the mucosal layer of the duodenum, such as to treat diabetes and/or obesity while leaving the duodenum anatomically connected after treatment. Replacement tissue can comprise cells that have migrated from one or more of: gastric mucosa; jejunal mucosa; an untreated portion of the duodenum whose mucosal tissue functions differently than the treated mucosal tissue functions prior to treatment; and combinations of these. Replacement tissue can include one or more tissue types selected from the group consisting of: scar tissue; normal intestinal mucosa; gastric mucosa; and combinations of these. In some embodiments, target tissue includes a treatment portion comprising the mucosal layer of the duodenum, and a safety-margin portion comprising a near-full or partial layer of the submucosal layer of the duodenum. In some embodiments, the target tissue comprises nearly the entire length of the mucosal layer of the duodenum, and can include a portion of the pylorus contiguous with the duodenal mucosa and/or a portion of the jejunum contiguous with the duodenal mucosa. Treatment of duodenal or other small intestine tissue can be performed to treat a disease and/or disorder selected from the group consisting of: diabetes; obesity; insulin resistance; a metabolic disorder and/or disease; and combinations of these. A near full circumferential portion (e.g. approximately 360°) of the mucosal layer of one or more segments of gastrointestinal tissue can be treated. In some embodiments, less than 360° of tubular tissue is treated, such as one or more circumferential portions less than 350°, or between 300° and 350°, such as to prevent a full circumferential scar from being created.

Target tissue can comprise tissue of the terminal ileum, such as to treat hypercholesterolemia and/or diabetes. In these embodiments, the target tissue can extend into the proximal ileum and/or the colon.

Target tissue can comprise gastric mucosal tissue, such as tissue regions that produce ghrelin and/or other appetite regulating hormones, such as to treat obesity and/or an appetite disorder.

Target tissue can comprise bladder wall tissue, such as to treat a disease and/or disorder selected from the group consisting of: interstitial cystitis; bladder cancer; bladder polyps; pre-cancerous lesions of the bladder; and combinations of these.

Target tissue can comprise tissue selected from the group consisting of: large and/or flat colonic polyps; margin tissue remaining after a polypectomy; and combinations of these. These tissue locations can be treated to treat residual cancer cells.

Target tissue can comprise airway lining tissue, such as to treat a disease and/or disorder selected from the group consisting of: bronchoalveolar carcinoma; other lung cancers; pre-cancerous lung lesions; and combinations of these.

Target tissue can comprise at least a portion of the intestinal tract afflicted with inflammatory bowel disease, such that Crohn's disease and/or ulcerative colitis can be treated.

Target tissue can comprise tissue of the oral cavity, such as to treat one or more of: oral cancers and a pre-cancerous lesion of the oral cavity.

Target tissue can comprise tissue of the nasopharynx, such as to treat nasal polyps.

Target tissue can comprise gastrointestinal tissue selected to treat Celiac disease and/or to improve intestinal barrier function.

The treatment assemblies, systems, devices and methods of the present inventive concepts can be constructed and arranged to avoid treating certain tissue, termed "non-target tissue" herein. Depending on the location of treatment, different non-target tissue can be applicable. In certain embodiments, non-target tissue can comprise tissue selected from the group consisting of: gastrointestinal adventitia; duodenal adventitia; the tunica serosa; the tunica muscularis; the outermost partial layer of the submucosa; Ampulla of Vater such as during mucosal treatment proximate the Ampulla of Vater; pancreas; bile duct; pylorus; and combinations of these.

As described herein, room pressure shall mean pressure of the environment surrounding the systems and devices of the present inventive concepts. Positive pressure includes pressure above room pressure or a pressure that is greater than another pressure, such as a positive differential pressure across a fluid pathway component such as a valve. Negative pressure includes pressure below room pressure or a pressure that is less than another pressure, such as a negative differential pressure across a fluid component pathway such as a valve. Negative pressure can include a vacuum but does not imply a pressure below a vacuum.

The treatment assemblies and expandable elements of the present inventive concepts can be constructed and arranged to automatically and/or manually expand in at least a radial direction. Typical expandable elements include but are not limited to: an inflatable balloon; a radially expandable cage or stent; one or more radially deployable arms; an expandable helix; an unfurlable compacted coiled structure; an unfurlable sheet; an unfoldable compacted structure; and combinations of these. In some embodiments, the expandable elements can comprise a radially expandable tube, such as a sheet of material resiliently biased in a radially expanded condition that can be compacted through a furling operation, or a sheet of material resiliently biased in a radially compact condition that can be expanded through an unfurling operation. The expandable element can comprise a foldable sheet, such as a sheet constructed and arranged to be folded to be radially compacted and/or to be unfolded to radially expand.

Each of the expandable assemblies and treatment assemblies of the present inventive concepts can include one or more ablation elements, such as electrodes configured to deliver radiofrequency (RF) energy, or other functional elements such as are described in reference to the figures herebelow. The ablation or other functional elements can be mounted on, within (e.g. within the wall) and/or inside of an expandable element such as a balloon or expandable cage. The electrodes of the present inventive concepts comprise an electrically conductive element ("conductor") configured to deliver RF energy to tissue, either through direct contact and/or a capacitive coupling (e.g. electrical energy delivered through a gap and/or dielectric material, such as a dielectric covering positioned between the electrode and tissue to receive electrical energy from the electrode). The electrodes can comprise one or more electrically connected segments of conductive material, such as one or more electrically connected filaments that can be arranged in parallel with one or more electrically connected filaments of a separate (electrically isolated) electrode.

The balloons of the present inventive concepts can be divided into two general categories: those that are composed of a substantially elastic material, such as silicone, latex, low-durometer polyurethane, and the like; and those that are composed of a substantially inelastic material, such as polyethylene terephthalate (PET), nylon, high-durometer polyurethane and the like. A third category includes balloons which include both elastic and inelastic portions. Within the category of elastic balloons, two subcategories exist: a first sub-category wherein a combination of material properties and/or wall thickness can be combined to produce a balloon that exhibits a measurable pressure-threshold for inflation, i.e. the balloon becomes inflated only after a minimum fluidic pressure is applied to the interior of the balloon; and a second sub-category, wherein the balloon expands elastically until an elastic limit is reached which effectively restricts the balloon diameter to a maximum value. It will be understood that the individual properties of the balloons in each of these categories can be applied to one or more advantages in the specific embodiments disclosed herein, these properties integrated singly or in combination. By way of example only, one or more of the following configurations can be employed: a highly elastic balloon can be used to achieve a wide range of operating diameters during treatment, e.g. during operation a desired balloon diameter can be achieved by adjustment of a combination of fluid temperature and pressure; a substantially inelastic balloon or a balloon that reaches its elastic limit within a diameter approximating a target tissue diameter (e.g. a duodenal mucosal diameter) can be used to achieve a relatively constant operating diameter that will be substantially independent of operating pressure and temperature; a balloon with a pressure-threshold for inflation can be used to maintain an uninflated diameter during relatively low pressure conditions of fluid flow and then achieve a larger operating diameter at higher pressure conditions of flow. Pressure-thresholded balloons can be configured in numerous ways. In one embodiment, a balloon is configured to have a relatively thick wall in its uninflated state, such as to maximize an electrically and/or thermally insulating effect while the balloon is maintained in this uninflated state. The balloon can be further configured such that its wall thickness decreases during radial expansion (e.g. to decrease an electrically and/or thermally insulating effect). In another embodiment, a balloon is configured to have a relatively small diameter in its uninflated state (e.g. a diameter that is small relative to the inner diameter of tubular target tissue such as the diameter of the mucosal layer of duodenal wall tissue), such as to minimize or completely eliminate apposition between the balloon and the surrounding tissue to minimize RF and/or other energy transfer into the surrounding tissue until the balloon is fully inflated. In another embodiment, a balloon and an ablation system or device are configured to circulate a flow of hot fluid through the balloon (e.g. an elastic balloon or an inelastic balloon) at a sufficiently low enough pressure to prevent apposition of the balloon with target tissue, such as to pre-heat one or more surfaces of the ablation system or ablation device that are in fluid communication with the balloon. In this configuration, when the balloon is fully inflated, the temperature of the fluid of the balloon will be at a desired level or it will rapidly and efficiently reach the desired level for treatment (i.e. minimal heat loss to the fluid path components due to the pre-heating). These configurations provide a method of delivering energy to tissue with a hot fluid filled balloon, as well as a method of "thermal priming" prior to target tissue treatment, such as is described in applicant's co-pending U.S. Provisional Application Ser. No. 61/635,810, entitled "Tissue Expansion Devices, Systems and Methods", filed Apr. 19, 2012, the contents of which is incorporated herein by reference in its entirety.

Treatment Modality 1: APPOSITION BETWEEN A TREATMENT ASSEMBLY AND THE TARGET TISSUE IS ESTABLISHED BY ADJUSTING THE TREATMENT ASSEMBLY DIAMETER. At times during treatment when it is desirable to increase or otherwise modify energy transfer between an ablation element such as an electrode and the target tissue, the treatment assembly diameter (e.g. the diameter of a balloon, deployable cage, expandable tube or other expandable assembly) can be increased in situ so as to conform to the native diameter of the target tissue, such as to the native diameter of tubular tissue such as small intestine wall tissue, such as duodenal wall tissue. At times during treatment when it is desirable to stop or otherwise decrease energy delivery between the treatment assembly and the target tissue, the treatment assembly diameter can be reduced in situ, such as to prevent or reduce contact of one or more ablation elements (e.g. electrodes or hot fluid filled balloons) with the target tissue. For those cases where the native diameter of the tissue varies substantially within the treatment zone, then a highly elastic or compliant balloon or other expandable element can be employed, such as a balloon or deployable cage which can be adjusted to achieve a wide range of operating diameters.

Treatment Modality 2: APPOSITION BETWEEN THE TREATMENT ASSEMBLY AND THE TARGET TISSUE IS ESTABLISHED BY CONTROLLING THE DIAMETER OF THE TARGET TISSUE. To initiate and/or increase energy delivery between a treatment assembly and the target tissue, the diameter of the target tissue can be decreased in situ so as to approximate and/or conform to the current diameter of the treatment assembly. To stop or otherwise decrease energy delivery between the treatment assembly and the target tissue, the diameter of the target tissue can be increased in situ, so as to prevent or reduce contact of tissue (e.g. target tissue and/or non-target tissue) with a treatment assembly. The diameter of the tissue proximate a treatment assembly can be increased or decreased, independent of the treatment assembly diameter, by means of delivering and/or withdrawing a fluid, to and/or from a lumen surrounded by target tissue, such as by using standard gastrointestinal insufflation techniques. Typical insufflation fluids include but are not limited to: gases such as carbon dioxide or air; liquids such as water or saline solution; and combinations of these. The insufflation fluids can be introduced through the ablation device, through an endoscope such as an endoscope through which the ablation device is inserted, and/or via another device placed proximate the target tissue. Delivery of insufflation fluids can be performed to manipulate tissue, such as to distend and/or elongate tissue. Alternatively or additionally, delivery of insufflation fluids can be performed to move target tissue away from a treatment assembly, such as to stop transfer of energy to target tissue at the end of a thermal dose period as described above. Removal of these insufflation fluids and/or the application of a vacuum or other negative pressure by one or more of the devices described hereabove, can be used to decrease the diameter of the target tissue, such as to bring the target tissue in contact with a treatment assembly. In this tissue diameter controlled approach, a balloon that can be maintained at a substantially constant diameter can be desirable, such as a substantially inelastic balloon such as a balloon with an elastic-limit.

Referring now to FIG. 1, a system for ablating or otherwise treating target tissue is illustrated, consistent with the present inventive concepts. System 10 is constructed and arranged to treat target tissue TT, which includes one or more tissue portions within a body lumen of a mammalian patient, such as a continuous circumferential segment of a duodenum or other small intestine location. In some embodiments, target tissue TT comprises a treatment portion comprising small intestine mucosal tissue (e.g. duodenal mucosal tissue) and a safety-margin portion comprising at least an innermost layer of the small intestine submucosa (e.g. an innermost layer of the duodenal submucosa). System 10 can be constructed and arranged to treat mucosal tissue while avoiding damage to adventitial tissue. System 10 can include one or more ablation catheters or other ablation devices, such as first ablation device 100 and second ablation device 100'. A supply of electrical energy is provided to at least ablation device 100 by energy delivery unit (EDU) 330, typically a supply of radiofrequency (RF) energy. A device for delivering fluid, fluid delivery unit 340, can be included in system 10, such as to deliver one or more fluids (e.g. one or more cooling and/or warming fluids) to modify the temperature of tissue and/or modify the temperature of one or more system device components. A controlling interface, controller 360 can be operably attached to one or more components of system 10, such as EDU 330, fluid delivery unit 340 and/or another device or assembly of system 10, such as to control and/or monitor one or more parameters of the attached device or assembly.

In the embodiment of FIG. 1, ablation device 100 includes coaxial shafts 111*a* and 111*b*. Shaft 111*b* has a distal end 112. Shafts 111*a* and 111*b* are sized and configured such that shaft 111*a* slidingly receives shaft 111*b*, such that they can be advanced and/or retracted in unison or independently. In some embodiments, device 100 comprises a flexible portion (e.g. a portion of shafts 111*a* and 111*b* including distal end 112) with a diameter less than 6 mm. In some embodiments, the flexible portion comprises a diameter less than 4.2 mm, less than 3.8 mm, less than 3.2 mm or less than 2.8 mm, such as to be slidingly received by a working channel of an endoscope that accepts diameters less than 6 mm. In some embodiments, device 100 comprises a shaft length of 100 cm or longer, or otherwise comprises a length sufficient to be orally and/or nasally inserted to reach the esophagus, stomach, duodenum, jejunum or terminal ileum of a patient. In FIG. 1, shafts 111*a* and 111*b* have been inserted through a working channel (e.g. a 6 mm working channel), lumen 351, of endoscope 350, typically a gastrointestinal endoscope. Shafts 111*a* and/or 111*b* can be inserted over a standard interventional guidewire, such as guidewire 371 shown exiting distal end 112 of shaft 111*b*. In an alternative embodiment, shafts 111*a* and 111*b* are positioned in a side-by-side configuration, such as to be placed in two separate lumens of endoscope 350 or in two other non-coaxial locations. In some embodiments, one or both of shafts 111*a* or 111*b* can be inserted alongside endoscope 350 (i.e. not through lumen 351, traveling parallel with but external to endoscope 350). Shaft 111*a* and 111*b* can include deflection means constructed and arranged to steer a distal portion of the shaft, such as is described in reference to FIGS. 9A-9C herebelow.

Ablation device 100 further includes two radially expandable assemblies, expandable assembly 130*a*, and expandable assembly 130*b*, mounted to shafts 111*a* and 111*b*, respectively. Expandable assemblies 130*a* and 130*b* can be constructed and arranged in one or more various forms to treat, modify, measure and/or diagnose target tissue TT and/or other tubular tissue. Expandable assemblies 130*a* and 130*b* can comprise an expandable element selected from the group consisting of: an inflatable balloon; a radially expandable stent or cage; an array of splines; one or more radially deployable arms; a spiral or other helical structure; a furlable structure such as a furlable sheet; an unfurlable structure such as an unfurlable sheet; a foldable structure such as a foldable sheet; an unfoldable structure such as an unfoldable sheet; and combinations of these. Expandable assembly 130*a* can be positioned proximal to expandable assembly 130*b* as shown in FIG. 1, or alternatively, expandable assembly 130*b* can be positioned proximal to expandable assembly 130*a*, such as when expandable assembly 130*a* is mounted to shaft 111*b* and expandable assembly 130*b* is mounted to shaft 111*a*.

In some embodiments, expandable assembly 130*a* and/or 130*b* comprise a length of at least 10 mm, such as a length between 10 mm and 40 mm, a length between 15 mm and 30 mm, or a length between 20 mm and 25 mm. In some embodiments, expandable assembly 130*a* and/or 130*b* comprise a length less than or equal to 15 mm, such as when configured to treat curvilinear portions of the gastrointestinal tract. Multiple expandable assemblies (e.g. between two and twenty expandable assemblies), such as expandable assemblies 130*a* and 130*b*, can be separated along a shaft by a distance less than or equal to 25 mm, such as a distance less than or equal to 20 mm. In some embodiments, expandable assembly 130*a* comprises a length, and the separation distance between expandable assembly 130*a* and 130*b* is less than or equal to the expandable assembly 130*a* length. In these embodiments, expandable assembly 130*b* can comprise a similar length to that of expandable assembly 130*a*, such as when both expandable assembly 130*a* and expandable assembly 130*b* comprise ablation elements.

Expandable assembly 130*a* and/or 130*b* can be constructed and arranged to expand to a diameter of at least 15 mm, such as a diameter of at least 20 mm, 25 mm or at least 30 mm. Expandable assembly 130*a* and/or 130*b* can be resiliently biased, such as in a radially expanded or radially compacted state. Expandable assembly 130*a* and/or 130*b* can be expanded and/or compacted by a control shaft, not shown but described in detail in reference to FIG. 10 herebelow. Expandable assembly 130*a* and/or 130*b* can be constructed and arranged to achieve a round or non-round shape (e.g. an oval or football shape) when expanded. Expandable assembly 130*a* and/or 130*b* can approximate a tube shape when expanded, such as a unidiameter or varying diameter tube shape. A tissue contacting portion of expandable assembly 130*a* and/or 130*b* can comprise a shape selected from the group consisting of: triangle; rectangle; pentagon; hexagon; trapezoid; and combinations of these, examples of which are described in reference to FIGS. 9A-9C herebelow. Expandable assembly 130*a* and/or 130*b* can be constructed and arranged to unfold to a radially expanded state, or to fold to a radially compacted state, such as is described in reference to FIG. 4A-4C herebelow.

Expandable assembly 130*a* can comprise at least one functional element 131*a*, and expandable assembly 130*b* can comprise at least one functional element 131*b*. Functional elements 131*a* and/or 131*b* can be elements selected from the group consisting of: an ablation element such as one or more electrodes constructed and arranged to deliver electrical energy such as radiofrequency (RF) energy; a sensor; a transducer; a fluid delivery element such as a needle, a fluid jet, a permeable membrane and/or an exit port; and combinations of these.

In some embodiments, expandable assembly 130*a* is constructed and arranged to ablate tissue, and expandable assembly 130*b* is constructed and arranged to perform at least one non-ablative function. Expandable assembly 130b can be constructed and arranged to occlude or partially occlude a lumen surrounded by tissue, such as a lumen of the gastrointestinal tract to be occluded during an insufflation procedure. Expandable assembly 130b can be constructed and arranged to manipulate tissue, such as to linearize and/or distend gastrointestinal tissue by frictionally engaging (e.g. when expanded) and applying forces to the tissue (e.g. by advancing and/or retracting shaft 111b). Expandable assembly 130b can be constructed and arranged to test and/or diagnose tissue, such as when expandable assembly 130b is used to measure a diameter of tubular tissue into which it has been inserted. Diameter measurements can be performed in various ways, including but not limited to: injection of a radiopaque fluid into assembly 130b and fluoroscopic measurement of the injected fluid; controlled inflation of assembly 130b to a pressure whose level corresponds to a luminal diameter; and combinations of these. In some embodiments, system 10 includes a separate device, such as a balloon catheter, used to perform a diameter measurement. One or more energy delivery parameters can be adjusted based on the measured diameter of target tissue and/or a target tissue portion.

In some embodiments, expandable assembly 130b is constructed and arranged to expand or otherwise modify one or more layers of tissue, such as to when functional element 131b comprises one or more needles and/or one or more water jets constructed and arranged to expand submucosal tissue of the gastrointestinal tract. Alternatively or additionally, system 10 can include a separate tissue expansion device, tissue expansion device 390. Expandable assembly 130b and/or tissue expansion device 390 can be constructed and arranged as is described in applicant's co-pending International Application Serial Number PCT/US2013/37485, entitled "Tissue Expansion Devices, Systems and Methods", filed Apr. 19, 2013, the contents of which is incorporated herein by reference in its entirety. Expandable assembly 130b and/or tissue expansion device 390 can include single or multiple fluid delivery elements, such as one or more needles and/or one or more water jets configured to deliver a fluid, gel or other material into tissue. Tissue expansion device 390 includes fluid delivery element 391, which can be attached to a radially expandable assembly, such as expandable assembly 393. Expandable assembly 393 can comprise an expandable balloon. Alternatively or additionally, expandable assembly 130b can include a fluid delivery element, such as fluid delivery element 129 as shown. Fluid delivery elements 391 and/or 129 can be attached to one or more fluid delivery tubes, not shown but attachable to a source of fluid. Fluid delivery elements 391 and/or 129 can be constructed and arranged to cause a circumferential expansion of tissue, such as a circumferential expansion of submucosal tissue of the duodenum or other small intestine location. Fluid delivery elements 391 and/or 129 can comprise an array of fluid delivery elements, such as a circumferential or linear array of needles and/or water jets. A vacuum can be applied proximate fluid delivery elements 391 and/or 129 to stabilize, manipulate or otherwise apply a force to the tissue receiving the expansion material. A vacuum can be applied via a port proximate the fluid delivery element, such as vacuum port 392 positioned proximate fluid delivery element 391. Tissue expansion can greatly alleviate the need for precision of treatment, such as precision of energy delivery, due to the increased size (e.g. increased depth) of the target tissue including an associated safety-margin of tissue to which treatment causes no significant adverse event (e.g. an expanded submucosal layer prior to a mucosal layer ablation). Treatment of target tissue after submucosal expansion is described in reference to FIG. 2 herebelow.

Expandable assembly 130a of FIG. 1 includes an ablation element comprising a pair of electrodes, first electrode 136a and second electrode 137a. In some embodiments, three or more electrodes can be included, such as an expandable assembly 130a which includes at least 4 electrodes. Electrodes 136a and/or 137a can be mounted on, within and/or inside of expandable assembly 130a. Electrodes 136a and/or 137a can be positioned to directly contact tissue for RF energy delivery, or they can be separated by a gap and/or dielectric material allowing capacitive coupling transfer of RF energy to tissue.

Electrodes 136a and/or 137a can comprise multiple elongate conductors, such as multiple elongate copper conductors in the interdigitated, parallel arrangement shown in FIG. 1. Electrodes 136a and/or 137a can comprise flexible conductors, such as flexible copper conductors that flex as expandable assembly 130a transitions between radially compacted and radially expanded conditions. Electrodes 136a and 137a can be attached to expandable assembly 130a with one or more attachment elements such as at least one of: a glue joint; a weld; a swage or a molecular bond. Electrodes 136a and 137a can be at least partially embedded in a portion of expandable assembly 130a, such as within the wall of a balloon when expandable assembly 130a comprises an inflatable balloon. Expandable assembly 130a can comprise a flexible substrate to which electrodes 136a and 137a are attached, such as the flexible substrate described in reference to FIG. 8A herebelow. Electrodes 136a and/or 137a can comprise a wire construction, such as a copper and/or other conductive wire with a diameter less then 500 microns. Electrodes 136a and/or 137a can include one or more anti-stick coatings and/or coverings, such as a coating and/or covering including polytetrafluoroethylene.

In some embodiments, expandable assemblies 130a and/or 130b comprise a shape that can be adjusted by an operator, such as via a control rod as is described in reference to Fig. and 10 herebelow. In some embodiments, the shape of the arrangement of electrodes 136a and/or 137a (e.g. arrangement between two separate electrodes and/or arrangement of conductors within a single electrode) can be operator modified by adjusting the shape of expandable assembly 130a.

Figure 10:
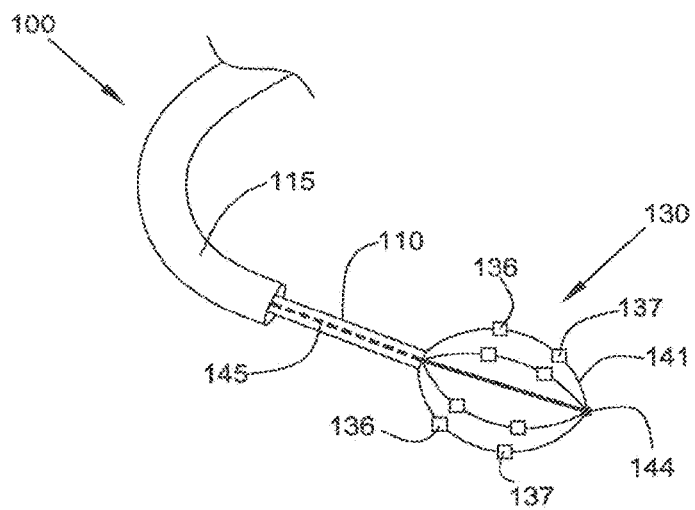
FIG. 10 is a distal portion of an ablation device comprising multiple spline-mounted electrodes, consistent with the present inventive concepts.
Figure 10A:
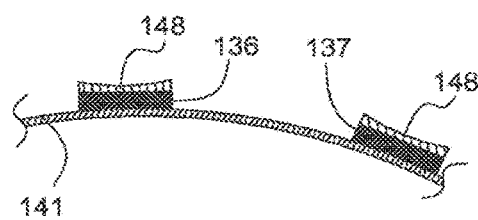
FIG. 10A is a side sectional view of dielectric covered electrodes mounted on a spline, consistent with the present inventive concepts.

Electrodes 136a and 137a can comprise capacitively coupled electrodes, such as those described in reference to FIG. 10A herebelow. Electrodes 136a and/or 137a can be constructed and arranged to transfer RF energy to the target tissue via a capacitive coupling including a gap and/or dielectric material between the electrode and the target tissue. A dielectric sheet or other covering can be included, with uniform or non-inform thickness. In some embodiments, a non-uniform thickness comprising thicker edge portions than middle portions can be included, such as to tend to create a uniform ablation depth (e.g. minimizing undesired edge effects along an electrodes perimeter).

Electrode 136a is electrically attached to wire 138a and electrode 137a is electrically attached to wire 139a. Wires 138a and 139a travel proximally within shaft 111b and are electrically attached to EDU 330, via one or more connections such as one or more operator attachable plugs and/or other electromechanical connections. System 10 can include ground pad 332, such as a standard RF energy delivery ground pad typically placed on the patient's back, such that EDU 330 can supply RF energy to electrodes 136a, 137a and/or any other electrodes of system 10 in monopolar, bipolar and/or combined monopolar-bipolar modes. Electrodes 136a and/or 137a can be configured to ablate various thickness of gastrointestinal tissue, such as at least the innermost 500 microns of small intestine tissue (e.g. at least the innermost 500 microns of duodenal tissue). Electrodes 136a and 137a can be configured to ablate a volume of tissue comprising a surface area and a depth, where the ratio of depth to surface area is less than or equal to 1 to 100 (e.g. less than 1%), or less than or equal to 1 to 1000 (e.g. less than 0.1%). In some embodiments, expandable assemblies 130a and/or 130b are constructed and arranged to be in a relatively rigid state, such as during delivery of electrical energy to target tissue TT. The rigidity can be used to maintain a pre-determined spacing of one or more conductors delivering RF energy, such as the spacing between parallel, neighboring conductors of electrodes 136a and 137a.

Electrodes 136a, 137a and/or other ablation elements of the present inventive concepts can include copper and/or other conductive materials arranged in various patterns, such that EDU 330 can deliver bipolar energy in associated patterns. Bipolar RF energy can be delivered between a first elongate conductor (e.g. of electrode 136a) and a second elongate conductor (e.g. of electrode 137a), such as two filaments positioned directly next to each other, or two filaments separated by one or more other conductors (e.g. separated by a conductor electrically isolated from the two filaments receiving the bipolar RF energy current delivered by EDU 330). In some embodiments, electrical energy is delivered between two elongate conductors, such as the pairs of conductors of electrodes 136a and 137a shown, where the spacing between the edges of two neighboring conductors of electrodes 136a and 137a (hereinafter the "edge-to-edge spacing" as illustrated in FIG. 2A) is between 200 micron and 2 mm. In some embodiments, the edge-to-edge spacing is less than or equal to 1.5 mm, such as less than 1.0 mm or less than 750 microns.

Electrodes 136a, 137a and/or other ablation elements of the present inventive concepts can comprise one or more elongate conductors with a width less than 2.0 mm, such as a width less than 1.5 mm, less than 1.0 mm or between 400 and 700 microns. In some embodiments, at least one electrode comprises one or more elongate conductors with a width of at least 230 microns. In some embodiments, at least one electrode comprises an elongate conductor with a width of at least 400 microns, such as a pair of electrodes comprising a pair of conductors with an edge-to-edge spacing of approximately 600 microns. In some embodiments, at least one electrode comprises an elongate conductor with a width of at least 700 microns, such as a pair of electrodes comprising a pair of conductors with an edge-to-edge spacing of approximately 400 microns. In some embodiments, at least one electrode comprises an elongate conductor with a width whose value is less than or equal to a desired depth of ablation. In some embodiments, a first electrode comprises a first conductor, and a second electrode comprises a second conductor, and the first conductor and the second conductor (hereinafter a "conductor pair" as illustrated in FIG. 2A) have an edge-to-edge spacing that is less than or equal to the desired depth of ablation. In some embodiments, conductor pairs have an edge-to-edge spacing between 230 microns and 2.0 mm, such as a spacing between 400 microns and 600 microns. In some embodiments, at least one conductor of a conductor pair has a width approximately 50% of the edge-to-edge spacing of that conductor pair. In some embodiments, multiple conductor pairs have similar edge-to-edge spacing, such as an edge to edge spacing with a uniformity greater than or equal to 95%, or greater than or equal to 98%.

Electrodes 136a, 137a and/or other ablation elements of the present inventive concepts can be arranged in an array of electrically connected or electrically isolated conductors, such as a circumferential array of linear and/or curvilinear elongate conductors. The circumferential array can comprise a partial circumferential array of conductors (e.g. as is shown in FIG. 1) such as an array covering approximately 45° to 300° of circumferential area. Partial circumferential arrays of conductors can treat a first target tissue portion and a second target tissue portion in two sequential steps, wherein the array is rotated between energy deliveries. Alternatively, the circumferential array can comprise a full 360° array of conductors (e.g. a full 360° array of interdigitated pairs of conductors comprising a single or multiple pairs of electrodes), such that a full circumferential volume of target tissue can be treated in a single energy delivery or in multiple energy deliveries that do not require repositioning of ablation device 100. In some embodiments, the circumferential array can be constructed and arranged to avoid creation of a full circumferential scar in tubular tissue, such as an array of between 300° and 350° of one or more electrodes (e.g. a 300° to 350° array of interdigitated pairs of conductors comprising a single or multiple pairs of electrodes). Two or more electrodes can be arranged in a helical array of two or more conductors. Two or more pairs of single or multiple filament conductors can be included, with any combination or arrangement of pairs driven by bipolar RF energy to treat the target tissue. In some embodiments, at least three, four or five pairs of conductors are driven simultaneously or sequentially by bipolar RF energy to treat the target tissue.

Electrodes 136a, 137a and/or other ablation elements of the present inventive concepts can comprise a sufficient length (singly or in combination) to treat substantially the entire length of the target tissue simultaneously or at least without having to reposition ablation device 100. In some embodiments, the target tissue comprises substantially the entire length of the duodenum. Electrodes 136a, 137a and/or other ablation elements of the present inventive concepts can comprise a sufficient length (singly or in combination) to treat at least 50% of the entire length of the target tissue simultaneously or at least without having to reposition ablation device 100. In some embodiments, the target tissue comprises at least 50% of the length of the duodenum. Electrodes 136a, 137a and/or other ablation elements of the present inventive concepts can be constructed and arranged to treat a first portion of target tissue followed by a second portion of target issue. The first and second treated tissue portions can be overlapping and they can have non-parallel central axes (e.g. tissue portions in a curved portion of the duodenum or other small intestine location). Three or more target tissue portions can be treated, such as to cumulatively ablate at least 50% of the duodenal mucosa.

In some embodiments, functional element 131b of expandable assembly 130b comprises one or more electrical energy delivery or non-electrical energy delivery ablation elements, such as those described in applicant's co-pending International PCT Application Serial Number PCT/US12/21739, entitled "Devices and Methods for the Treatment of Tissue", filed Jan. 18, 2012, the contents of which is incorporated herein by reference in its entirety. In some embodiments, functional element 131b comprises an ablation element selected from the group consisting of: an RF energy delivery element such as one or more electrodes, each comprising one or more elongate conductors; an ultrasonic transducer such as one or more piezo crystals configured to ablate tissue; a laser energy delivery element such as one or more optical fibers and/or laser diodes; a heat delivery element such as a hot fluid filled balloon; a rotating ablation element; a circumferential array of ablation elements; and combinations of these. In these embodiments, either or both expandable assembly 130a and 130b can be used to ablate target tissue TT.

In some embodiments, expandable assemblies 130a and/or 130b comprise inflatable or otherwise expandable balloons, such as one or more of: a compliant balloon; a non-compliant balloon; a balloon with a pressure threshold; a balloon with compliant and non-compliant portions; a balloon with a fluid entry port; a balloon with a fluid exit port; and combinations of these. In some embodiments, expandable assemblies 130a and/or 130b comprise a balloon which is fluidly attached to an inflation tube, such as an inflation tube which travels proximally through shaft 111a and/or 111b and is attached to an inflation port, not shown but typically attached to a handle on the proximal end of ablation device 100.

In some embodiments, expandable assembly 130b comprises an abrasive element configured for abrading target tissue, such as an abrasive element attached to a balloon or expandable cage.

Shafts 111a and 111b can include one or more lumens passing therethrough, and can comprise wires and/or optical fibers for transfer of data and/or energy such as RF energy to electrodes 136a and 137a of assembly 130a. Shafts 111a and/or 111b can comprise one or more shafts, such as one or more concentric shafts configured to deliver and/or re-circulate hot and/or cold fluid through expandable assemblies 130a and/or 130b, respectively, such as to deliver a bolus of hot fluid energy and/or other thermal dose as described in applicant's co-pending International Application Serial Number PCT/US2013/28082, entitled "Heat Ablation Systems, Devices and Methods for the Treatment of Tissue", filed Feb. 27, 2013, the contents of which is incorporated herein by reference in its entirety. Device 100 can comprise a single expandable assembly 130a, without inclusion of expandable assembly 130b, as is described in reference to multiple embodiments herebelow.

Figure 3:
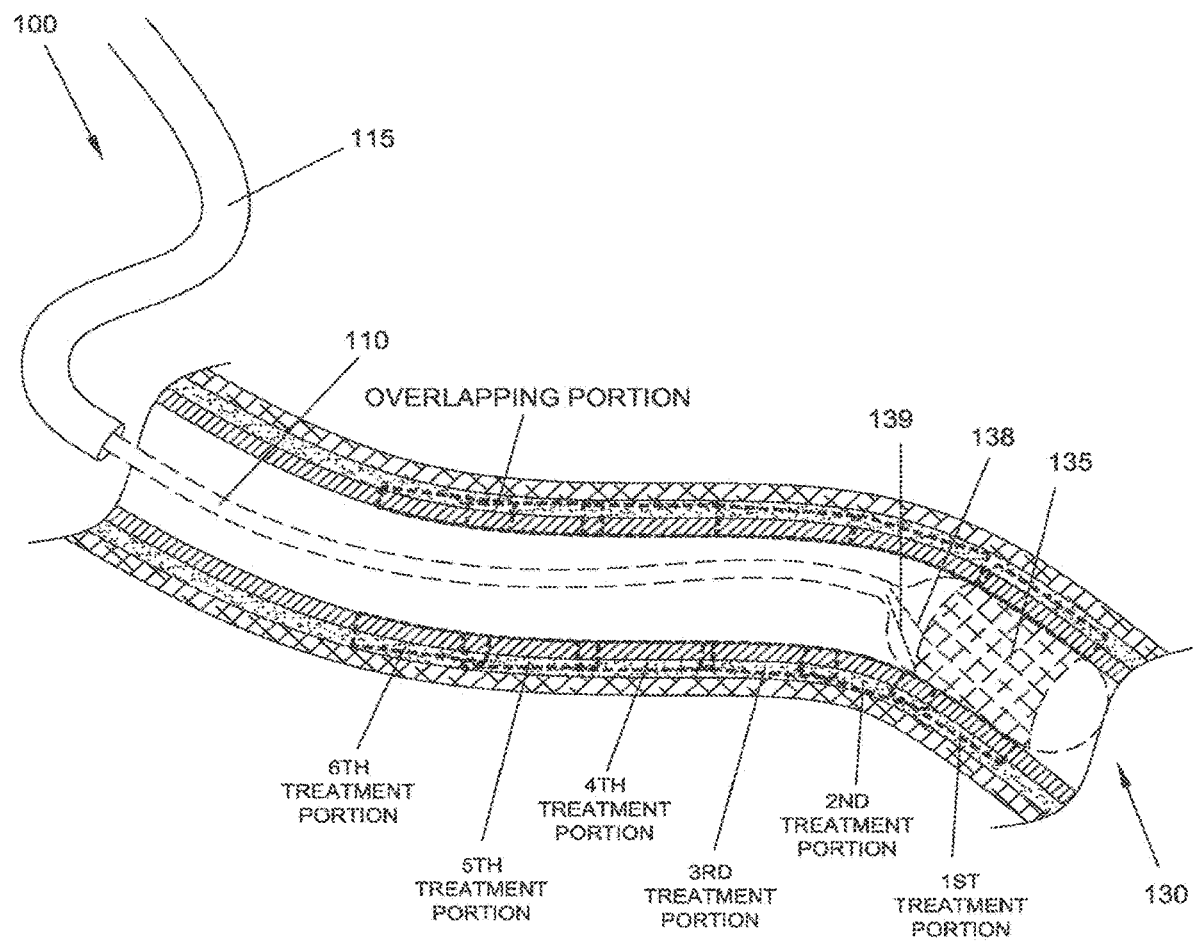
FIG. 3 is a side sectional view of the distal portion of an ablation device inserted into a curvilinear section of duodenum, consistent with the present inventive concepts.

Expandable assembly 130a and/or 130b can be constructed and arranged to ablate tissue or otherwise perform a function while positioned in a curved segment of the gastrointestinal tract, such as is described in reference to FIG. 3 herebelow.

The systems of the prevent inventive concepts are constructed and arranged to ablate or otherwise treat target tissue TT, such as duodenal or other small intestinal mucosal tissue, while avoiding damaging non-target tissue, such as the gastrointestinal adventitia. Target tissue TT can include at least a portion of safety-margin tissue comprising tissue whose ablation causes minimal or no adverse effect to the patient, such as sub-mucosal tissue of the gastrointestinal tract. Target tissue TT can comprise one or more portions of tissue that are treated simultaneously or sequentially. In some embodiments, the target tissue TT comprises the majority of the length of the duodenal mucosa, such as at least 50% of the duodenal mucosa. In some embodiments, the target tissue TT comprises at least 90% of the duodenal mucosa, or at least 95% of the duodenal mucosa. In some embodiments, the target tissue TT includes the full mucosal thickness of at least a portion of duodenal or other small intestinal tissue, as well as at least the innermost 100 microns of submucosal tissue, or at least the innermost 200 microns of submucosal tissue. In some embodiments, system 10 and/or ablation device 100 is constructed and arranged to avoid ablating at least an outermost layer of small intestine submucosal tissue (e.g. avoid ablating an outermost layer of duodenal submucosal tissue), such as a non-ablated outermost layer that is at least 100 microns thick, or at least 200 microns thick. The target tissue TT can include at least one of ileal mucosal tissue or gastric mucosal tissue.

Endoscope 350 can be a standard endoscope, such as a standard gastrointestinal endoscope, or a customized endoscope, such as an endoscope including sensor 353 configured to provide information related to the tissue treatment of the present inventive concepts. Endoscope 350 can include camera 352, such as a visible light, ultrasound and/or other visualization device used by the operator of system 10 prior to, during and/or after the treatment of target tissue TT, such as during insertion and/or removal of endoscope 350 and/or shafts 111a and 111b of ablation device 100. Camera 352 can provide direct visualization of internal body spaces and tissue, such as the internal organs of the gastrointestinal tract. Endoscope 350 can be coupled with or otherwise include a guidewire, e.g. guidewire 371, such as to allow insertion of endoscope 350 into the jejunum.

System 10 can be constructed and arranged to perform insufflation of a body lumen, such as a segment of the gastrointestinal tract. The body lumen can be pressurized, such as by using one or more standard insufflation techniques. Insufflation fluid can be introduced through second lumen 354 of endoscope 350. Second lumen 354 travels proximally and connects to a source of insufflation liquid and/or gas, such as fluid delivery unit 340, and typically a source of air, carbon dioxide, water and/or saline. Alternatively or additionally, insufflation fluid can be delivered by ablation device 100, such as through shaft 111a and/or 111b, and/or through a port in expandable assembly 130a and/or 130b, such as when functional elements 131a and/or 131b, respectively, comprise a fluid delivery port attached to a source of insufflation liquid and/or gas. Alternatively or additionally, a separate device configured to be inserted through endoscope 350 and/or to be positioned alongside endoscope 350, can have one or more lumens configured to deliver the insufflation fluid. System 10 can include one or more occlusive elements and/or devices, such as expandable assemblies 130a, 130b and/or another expandable device configured to radially expand such as to fully or partially occlude a body lumen, such that insufflation pressure can be achieved and/or maintained over time (e.g. reduce or prevent undesired migration of insufflation fluid). The one or more occlusive elements and/or devices can be positioned proximal to and/or distal to the luminal segment to be insufflated.

Functional element 131a and/or functional element 131b can comprise a sensor. In some embodiments, functional element 131a, functional element 131b, sensor 353 and/or another sensor of system 10 can comprise a sensor selected from the group consisting of: temperature sensors such as thermocouples, thermistors, resistance temperature detectors and optical temperature sensors; strain gauges; impedance sensors such as tissue impedance sensors; pressure sensors; blood sensors; optical sensors such as light sensors; sound sensors such as ultrasound sensors; electromagnetic sensors such as electromagnetic field sensors; and combinations of these. The sensors can be configured to provide information to one or more components of system 10, such as to controller 360 and/or EDU 330, such as to monitor the treatment of target tissue TT and/or to treat target tissue TT in a closed loop configuration. Energy delivery from EDU 330 can be modified based on one or more sensor readings. In one embodiment, an algorithm of controller 360 and/or EDU 330 processes one or more sensor signals to modify amount of energy delivered, power of energy delivered, voltage of energy delivered, current of energy delivered and/or temperature of energy delivery.

A sensor such as a chemical detection sensor can be included, such as to confirm proper apposition of expandable assemblies 130a and/or 130b. In this configuration, a chemical sensor such as a carbon dioxide sensor can be placed distal to expandable assemblies 130a and/or 130b, and a fluid such as carbon dioxide gas is introduced proximal to the expandable assemblies 130a and/or 130b. Detection of the introduced fluid can indicate inadequate apposition of expandable assemblies 130a and/or 130b, such as to prevent inadequate transfer of energy to target tissue TT and/or prevent inadequate measurement, modification and/or diagnosis of target tissue TT.

Functional element 131a, functional element 131b, sensor 353 and/or another sensor of system 10 can comprise a sensor configured to provide information related to the tissue treatment performed by expandable assembly 130a and/or 130b, such as a visual sensor mounted to expandable assembly 130a that is configured to differentiate tissue types that are proximate expandable assembly 130a, such as to differentiate mucosal and submucosal tissue. Applicable visible sensors include but are not limited to: visible light camera; infrared camera; CT Scanner; MRI; and combinations of these. In some embodiments, electrical energy delivered by electrodes 136a, 137a and/or other ablation elements of system 10 is based on one or more signals from the visible sensor, such as a sensor providing a signal correlating to tissue color. Functional elements 131a and 131b can comprise a sensor configured to provide information related to the tissue treatment performed by expandable assembly 130a and/or 130b, such as a temperature sensor configured to monitor the temperature of treatment provided by expandable assembly 130a and/or tissue proximate expandable assembly 130a. Functional elements 131a and/or 131b can comprise multiple temperature sensors, such as multiple temperature sensors positioned on expandable assembly 130a and/or 130b, respectively, with a spacing of at least one sensor per square centimeter. RF and/or other energy delivered by EDU 330 can be based on signals recorded by the multiple temperature sensors.

Functional element 131a and/or functional element 131b can comprise a transducer. In these and other embodiments, functional element 131a, functional element 131b, and/or another transducer of system 10 can be a transducer selected from the group consisting of: a heat generating element; a drug delivery element such as an iontophoretic drug delivery element; a magnetic field generator; an ultrasound wave generator such as a piezo crystal; a light producing element such as a visible and/or infrared light emitting diode; and combinations of these.

EDU 330 is configured to deliver energy to one or more ablation elements of system 10. In some embodiments, EDU 330 is configured to deliver at least RF energy, and system 10 includes ground pad 332 configured to be attached to the patient (e.g. on the back of the patient), such that RF energy can be delivered in monopolar delivery mode to electrode 136a, 137a and/or another electrode of system 10. Alternatively or additionally, EDU 330 can be configured to deliver energy in a bipolar RF mode, such as bipolar energy delivered between electrodes 136a and 137a of expandable assembly 130a. Alternatively or additionally, EDU 330 can be configured to deliver energy in a combined monopolar-bipolar mode.

EDU 330 can be constructed and arranged to deliver RF and/or other forms of energy to one or more ablation elements of expandable assembly 130a and/or 130b. In some embodiments, EDU 330 delivers energy selected from the group consisting of: RF energy; microwave energy; plasma energy; ultrasound energy; light energy; and combinations of these. Energy can be continuous and/or pulsed, and can be delivered in a closed-loop fashion as described hereabove. Energy delivery parameters such as power, voltage, current and frequency can be held relatively constant or they can be varied by EDU 330. Energy delivery can be varied from a first tissue location (e.g. a first portion of target tissue) to a second location (e.g. a second portion of target tissue), such as a decrease in energy from a first treated location to a second treated location when the second treated location is thinner than the first treated location. Alternatively or additionally, energy delivery can be varied during a single application of energy to a single tissue location, such as by adjusting one or more energy delivery parameters during a continuous energy delivery.

System 10 can be further configured to deliver and extract one or more fluids from expandable assembly 130a and/or 130b, such as to pre-heat expandable assembly 130a and/or 130b and/or to deliver heat energy to target tissue TT via the delivered fluids. In one embodiment, fluid delivery unit 340 and/or EDU 330 are configured to deliver one or more supplies of hot fluid, such as hot water or saline when expandable assembly 130a and/or 130b comprises a balloon positioned at the end of one or more fluid delivery tubes, not shown but typically as described in applicant's co-pending International Application Serial Number PCT/US2013/28082, entitled "Heat Ablation Systems, Devices and Methods for the Treatment of Tissue", filed Feb. 27, 2013, the contents of which is incorporated herein by reference in its entirety. In these embodiments, fluid delivery unit 340 and/or EDU 330 typically includes one or more fluid pumps, such as one or more peristaltic, displacement and/or other fluid pumps; as well as one or more heat exchangers and/or other fluid heating elements internal and/or external to device 100. Fluid delivery unit 340 and/or EDU 330 can be constructed and arranged to rapidly deliver and/or withdraw fluid to and/or from expandable assemblies 130a and/or 130b via one or more fluid transport means. Fluid transport means can include a pump configured to deliver fluid at a flow rate of at least 50 ml/min and/or a pump and/or vacuum source configured to remove fluid at a flow rate of at least 50 ml/min. A pump and/or vacuum source can be configured to continuously exchange hot fluid and/or to perform a negative pressure priming event to remove fluid from one or more fluid pathways of device 100. Fluid delivery unit 340, EDU 330 and/or ablation device 100 can include one or more valves in the fluid delivery and/or fluid withdrawal pathways or one or more other valves in the fluid pathway within expandable assemblies 130a and/or 130b. Valves can be configured to control entry of fluid into an area and/or to maintain pressure of fluid within an area. Valves can be used to transition from a heating fluid, such as a fluid of 90° C. maintained in a treatment assembly for approximately 12 seconds, to a cooling fluid, such as a fluid between 4° C. and 10° C. maintained in the assembly element for approximately 30 to 60 seconds. Typical valves include but are not limited to: duck-bill valves; slit valves; electronically activated valves; pressure relief valves; and combinations of these. Fluid delivery unit 340 and/or EDU 330 can be configured to rapidly inflate and/or deflate expandable assemblies 130a and/or 130b. Fluid delivery unit 340 and/or EDU 330 can be configured to purge the fluid pathways of device 100 with a gas such as air, such as to remove cold and/or hot fluid from device 100 and/or to remove gas bubbles from device 100.

System 10 can include conductive gel 333, constructed and arranged to conduct thermal and/or electrical energy between a component of system 10 and tissue. Conductive gel 333 can be delivered by ablation device 100, such as via a port in expandable assembly 130a and/or 130b, not shown but typically connected to a fluid delivery tube that travels proximally to a handle on device 100, and/or via another device of system 10. Conductive gel 333 can be delivered to at least one of tissue or an external surface of a portion of a device of system 10, such as the external surface of expandable assembly 130a and/or 130b. Conductive gel 333 can be thermally conductive such as to improve heat transfer to tissue. Conductive gel 333 can be thermally conductive such as to improve cooling of tissue, such as when cool air is delivered to gel 333 and/or tissue via a component of system 10. Conductive gel 333 can be electrically conductive to improve transfer of electrical energy to tissue. System 10 can be constructed and arranged to allow an operator to place conductive gel 333 onto tissue prior to expansion of expandable assembly 130a and/or 130b. System 10 can be constructed and arranged to allow an operator to place conductive gel 333 onto electrode 136a and/or 137a prior to electrode 136a and/or 137a, respectively, contacting target tissue and/or delivering RF energy to tissue.

EDU 330, electrodes 136a and 137a and/or other components of system 10 can be constructed and arranged to treat target tissue TT with a non-desiccating ablation, such as by avoiding tissue temperatures above 100° C., avoiding the creation of steam, or otherwise avoiding deleterious desiccation of tissue. System 10 can be constructed and arranged to minimize heat production in the outermost 50% of a mucosal layer (e.g. to minimize RF current flow in the outermost 50% of a mucosal layer). In these embodiments, the outermost 50% of the mucosal layer can be ablated via thermal conduction (e.g. thermal conduction from the innermost 50% of the mucosal layer). Similarly, system 10 can be constructed and arranged to minimize heat production in the outermost 80% of a mucosal layer, such as to ablate the outermost 80% of the mucosal layer via thermal conduction. System 10 can be constructed and arranged to maximize the flow of current, such as through the innermost 50% of a mucosal layer, or through the innermost 20% of a mucosal layer. In some embodiments, system 10 can be constructed and arranged to avoid detachment of tissue particles.

EDU 330, electrodes 136a and 137a and/or other components of system 10 can be constructed and arranged to deliver RF energy to target tissue at a power density that averages less than 20 watts per $cm^2$, such as a power density that averages less than 10 watts per $cm^2$ or less than 4 watts per $cm^2$. RF energy can be delivered for a particular portion of target tissue for a time period of at least one second, such as a time period of at least 5 seconds, at least 10 seconds or at least 20 seconds. In some embodiments, RF energy is delivered to target tissue at a level that decreases (e.g. one or more energy delivery parameter levels decrease) over time. In some embodiments, RF energy delivery comprises a modulated energy delivery, such as a pulse width modulated energy delivery with an "on" portion of the duty cycle below 20%. In some embodiments, EDU 330 comprises an RF source comprising a 300 Watts or less RF source, such as a 150 Watts or less RF source. In some embodiments, EDU 330 is configured to deliver an instantaneous power of less than 300 Watts, or less than 260 Watts, such as an instantaneous power than decreases to zero Watts over approximately 30 seconds. In some embodiments, EDU 330 is configured to deliver RF energy in a current-driven mode. In some embodiments, EDU 330 is configured to deliver RF energy for at least 2 seconds, such as in a continuous and/or pulsed manner. In some embodiments, the frequency of RF energy is maintained below 1.0 Mhz.

EDU 330, electrodes 136a and 137a and/or other components of system 10 can be constructed and arranged to deliver RF energy to target tissue such that the temperature of at least a portion of the target tissue rises rapidly, such as at a rate of greater than or equal to 17.5° C. per second. The RF energy can be delivered to cause the temperature of at least a portion of the target tissue to reach a setpoint temperature between 60° C. and 90° C., such as a setpoint temperature between 65° C. and 80° C. System 10 can be constructed and arranged to cause the target tissue to elevate to a setpoint temperature and maintain that setpoint temperature, such as by maintaining the setpoint temperature for a time period between 2 and 40 seconds. In these embodiments, the setpoint temperature can be between 60° C. and 90° C., such as a setpoint temperature between 75° C. and 85° C. that is maintained for between 15 and 25 seconds. In some embodiments, after a setpoint temperature is achieved and/or maintained, the RF energy delivered causes a decrease in temperature over time, such as to match a tissue response of the target tissue.

Controller 360 can include a graphical user interface configured to allow one or more operators of system 10 to perform one or more functions such as entering of one or more system input parameters and visualizing and/or recording of one or more system output parameters. Controller 360 can include one or more user input components (e.g. touch screens, keyboards, joysticks, electronic mice and the like), and one or more user output components (e.g. video displays; liquid crystal displays; alphanumeric displays; audio devices such as speakers; lights such as light emitting diodes; tactile alerts such as assemblies including a vibrating mechanism; and the like). Examples of system input parameters include but are not limited to: type of energy to be delivered such as RF energy, thermal energy and/or mechanical energy; quantity of energy to be delivered such as a cumulative number of joules of energy to be delivered and/or peak amount of energy to be delivered; types and levels of combinations of energies to be delivered; energy delivery duration; pulse width modulation percentage of energy delivered; temperature of a fluid to be delivered to a expandable element such as a balloon; temperature of a cooling fluid to be delivered; flow rate of a hot fluid to be delivered; volume of a hot fluid to be delivered; number of reciprocating motions for an energy delivery element to transverse; temperature for a treatment assembly such as target temperature and/or maximum temperature; insufflation pressure; insufflation duration; and combinations of these. System input parameters can include information based on patient anatomy and/or conditions such as pre-procedural and/or peri-procedural parameters selected from the group consisting of: mucosal density and/or thickness; mucosal "lift" off of submucosa after a submucosal injection; longitudinal location of target tissue within the GI tract; and combinations of these. Examples of system output parameters include but are not limited to: temperature information such as tissue and/or treatment assembly temperature information; pressure information such as balloon pressure information and/or insufflation pressure information; force information such as level of force applied to tissue information; patient information such as patient physiologic information recorded by one or more sensors; and combinations of these.

Controller 360 and/or one or more other components of system 10 can include an electronics module, such as an electronics module including a processor, memory, software, and the like. Controller 360 can be configured to allow an operator to initiate, modify and cease treatment of target tissue by the various components of system 10, such as by controlling energy delivery unit 330 and/or fluid delivery unit 340. Controller 360 can be configured to modify one or more RF energy delivery parameters, such as a parameter selected from the group consisting of: voltage; current; frequency; pulse width modulation on-time and/or off-time; a time division multiplexing parameter; and combinations of these. Controller 360 can be configured for manual control, so that the operator first initiates the energy delivery, then allows the associated ablation element to ablate the tissue for some time period, after which the operator terminates the energy delivery.

Controller 360 and EDU 330 can be configured to deliver energy in constant, varied, continuous and discontinuous energy delivery profiles. Pulse width modulation and/or time division multiplexing (TDM) can be incorporated to achieve precision of energy delivery, such as to ensure ablation of target tissue while leaving non-target tissue intact.

In some embodiments, where system 10 is constructed and arranged to perform hot fluid ablation, controller 360 can be configured to adjust the temperature, flow rate and/or pressure of fluid delivered to expandable assembly 130a and/or 130b. Controller 360 can be configured to initiate insufflation and/or to adjust insufflation pressure. Controller 360 can be configured to deliver energy (e.g. from fluid delivery unit 340 and/or EDU 330) and/or other tissue treatment in a closed-loop fashion, such as by modifying one or more tissue treatment parameters based on signals from one or more sensors of system 10 such as those described hereabove. Controller 360 can be programmable such as to allow an operator to store predetermined system settings for future use.

Controller 360 can comprise an impedance monitoring assembly, such as an impedance monitoring assembly that receives impedance information from one or both of functional element 131a of expandable assembly 130a and/or functional element 131b of expandable assembly 130b. EDU 330 can deliver RF energy to electrodes 136a and/or 137a based on the impedance determined by the impedance monitoring assembly.

Numerous embodiments of the systems, methods and devices for treating target tissue described hereabove include controlling and/or monitoring the change in target tissue temperature to cause its ablation, such as a temperature increase above 43° C., typically above 60° C., 70° C. or 80° C., to ablate at least a portion of the target tissue TT. One or more cooling fluids can be delivered to limit or otherwise control ablation, such as to prevent damage to non-target tissue, such as the adventitial layer of the duodenum or other small intestine segment. Fluid delivery unit 340 can be constructed and arranged to deliver a fluid to tissue and/or a component and/or assembly of system 10, such as to warm and/or cool the tissue, component and/or assembly. Fluid delivery unit 340 can be configured to deliver a cooling fluid to a luminal wall such as a wall of the small intestine (e.g. a duodenal wall), such as prior to a delivery of RF energy, during a delivery of RF energy and/or after a delivery of RF energy. In some embodiments, a chilled fluid, such as a fluid below 20° C., or below 10° C. is used to cool tissue prior to, during and/or after delivery of RF energy to tissue. In some embodiments, the chilled fluid is delivered between ablation of a first portion of target tissue and a second portion of target tissue, such as to remove residual heat remaining after the first treatment. The cooling fluid can be delivered through functional element 131a of expandable assembly 130a and/or functional element 131b of expandable assembly 130b, such as when functional element 131a and/or 131b comprises a fluid delivery element such as a nozzle, an exit hole or a permeable membrane. The cooling fluid can be supplied to expandable assembly 130a and/or 130b, such as when expandable assembly 130a and/or 130b comprises a balloon configured to contact tissue. Alternatively or additionally, fluid delivery unit 340 can be fluidly attached to another component of ablation device 100 and/or system 10, the attached component not shown but configured to deliver fluid to tissue and/or a component of system 10 such as to add and/or absorb heat. Fluid delivery unit 340 can comprise a cryogenic source used to deliver fluids at low temperatures, such as temperatures below 0° C. Examples of fluids delivered include but are not limited to: liquids such as water and/or saline; gases such as carbon dioxide, nitrogen, nitrous oxide and/or air; and combinations of these. Fluid delivery unit 340 can include a desiccant and/or drying assembly configured to dehydrate or otherwise remove moisture from one or more delivered gases prior to their delivery.

System 10 can include a motion control mechanism, such as motion transfer assembly 335. Motion transfer assembly 335 can be constructed and arranged to rotate, translate and/or otherwise move a component of system 10, such as to move one or more of expandable assemblies 130a and/or 130b of ablation device 100. In some embodiments, motion transfer assembly 335 is configured to rotate and/or axially translate shafts 111a and/or 111b such that expandable assemblies 130a and/or 130b, respectively, are rotated and/or translated. Motion transfer assembly 335 can be configured to rotate expandable assemblies 130a and 130b independently or in unison. Motion transfer assembly 335 can be configured to translate expandable assembly 130a as RF energy is being delivered by at least one of electrodes 136a or 137a. Motion transfer assembly 335 can be configured to translate expandable assembly 130a between a first RF energy delivery and a second RF energy delivery. Motion transfer assembly 335 can include one or more rotational and/or linear drive assemblies, such as those including rotational motors, magnetic and other linear actuators, and the like which are operably connected to shaft 111a and/or 111b. Shafts 111a and/or 111b are constructed with sufficient column strength and/or torque transfer properties to sufficiently rotate and/or translate expandable assemblies 130a and/or 130b, respectively. Motion transfer assembly 335 can be in communication with controller 360, such as to activate, adjust and/or otherwise control motion transfer assembly 335 and thus the motion of expandable assemblies 130a and/or 130b. Motion transfer assembly 335 can be manually driven and/or automatically (e.g. motor) driven. Alternatively or additionally, motion transfer assembly 335 can be used to advance and/or retract expandable assemblies 130a and/or 130b from a first position to treat a first portion of target tissue, to a second position to treat a second portion of target tissue. In this embodiment, repositioning of expandable assemblies 130a and/or 130b can be configured to provide overlapping treatment, such as the overlapping treatment described in reference to FIG. 3 herebelow.

System 10 can include a second ablation device 100' constructed and arranged to treat target tissue TT. Second ablation device 100' can be of similar or dissimilar construction to ablation device 100. In some embodiments, second ablation device 100' comprises an expandable assembly with a different diameter than expandable assembly 130a of device 100. In some embodiments, second ablation device 100' comprises an electrode with a different pattern of conductors than electrode 136a and/or 137a of device 100. In some embodiments, second ablation device 100' comprises a device selected from the group consisting of: hot fluid filled balloon device; vapor ablation device; cryoablation device; laser ablation device; ultrasound ablation device; and combinations of these.

System 10 can further include one or more imaging devices, such as imaging device 370. Imaging device 370 can be configured to be inserted into the patient and can comprise a visual light camera; an ultrasound imager; an optical coherence domain reflectometry (OCDR) imager; and/or an optical coherence tomography (OCT) imager, such as when integral to, attached to, contained within and/or proximate to shaft 111a and/or 111b. Imaging device 370 can be inserted through a separate working channel of endoscope 350, lumen not shown. In one embodiment, imaging device 370 is an ultrasound transducer connected to a shaft, not shown but surrounded by shaft 111a and typically rotated and/or translated to create a multi-dimensional image of the area surrounding imaging device 370. Alternatively or additionally, imaging device 370 can be external to the patient, such as an imaging device selected from the group consisting of: an X-ray; a fluoroscope; an ultrasound image; an MRI; a PET Scanner; and combinations of these. Image and other information provided by imaging device 370 can be provided to an operator of system 10 and/or used by a component of system 10, such as controller 360, to automatically or semi-automatically adjust one or more system parameters such as one or more energy delivery parameters.

System 10 can further include protective element 380, constructed and arranged to be positioned on, over and/or otherwise proximate non-target tissue to prevent damage to the non-target tissue during energy delivery and/or other tissue treatment event. Protective element 380 can comprise an element selected from the group consisting of: a deployable and/or recoverable cap and/or covering; an advanceable and/or retractable protective sheath; and combinations of these. Protective element 380 can be delivered with endoscope 350 and/or another elongate device such that element 380 can be placed over or otherwise positioned to protect non-target tissue, such as tissue selected from the group consisting of: Ampulla of Vater, bile duct, pancreas, pylorus, muscularis externae, serosa; and combinations of these. In a typical embodiment, protective element 380 is removed within 24 hours of placement, such as by being removed during the procedure after treatment of the target tissue TT.

System 10 can be constructed and arranged to prevent excessive distension of a segment of the small intestine (e.g. a segment of the duodenum), such as to prevent application of a force that could cause tearing of the serosa. In some embodiments, system 10 is constructed and arranged such that all tissue contacting components and/or fluids delivered by system 10 maintain forces applied on a gastrointestinal wall below 2.5 psi, such as less than 1 psi. System 10 can be constructed and arranged such that one or more radial expandable assemblies 130 or other radial expandable assemblies or elements apply a force of at least 0.2 psi, such as a force of at least 0.5 psi, such as to improve the quality of apposition of the radially expandable element or assembly. System 10 can be constructed and arranged to avoid or otherwise minimize damage to the muscularis layer of the gastrointestinal tract, such as by controlling energy delivery and/or by minimizing trauma imparted by one or more components of system 10.

System 10 can further include one or more pharmaceutical and/or other agents 500, such as an agent configured for systemic and/or local delivery to a patient. Agents 500 can be delivered pre-procedurally, peri-procedurally and/or post-procedurally. Agents 500 can be configured to improve healing, such as agents selected from the group consisting of: antibiotics; steroids; mucosal cytoprotective agents such as sucralfate; proton pump inhibitors and/or other acid blocking drugs; and combinations of these. Alternative or in addition to agents 500, pre-procedural and/or post-procedural diets can be employed. Pre-procedural diets can include food intake that is low in carbohydrates and/or low in calories. Post-procedural diets can include food intake that comprise a total liquid diet and/or a diet that is low in calories and/or low in carbohydrates.

In some embodiments, system 10 does not include a chronically implanted component and/or device, such as where system 10 includes only body inserted devices that are removed at the end of the clinical procedure or shortly thereafter, such as devices removed within 8 hours of insertion, within 24 hours of insertion and/or within one week of insertion. In an alternative embodiment, implant 510 can be included. Implant 510 can comprise at least one of: a stent; a sleeve; and/or a drug delivery device such as a coated stent, a coated sleeve and/or an implanted pump. Implant 510 can be inserted into the patient and remain implanted for a period of at least one month, at least 6 months or at least 1 year.

Each of the components of system 10 can be removably attached to another component, particularly ablation device 100, controller 360, energy delivery unit 330, motion transfer element 335, fluid delivery unit 340, ground pad 332, endoscope 350 and/or second ablation device 100'. Typical attachment means include but are not limited to mechanical or electromechanical connectors providing an electrical, optical and/or fluidic connection.

Figure 2:
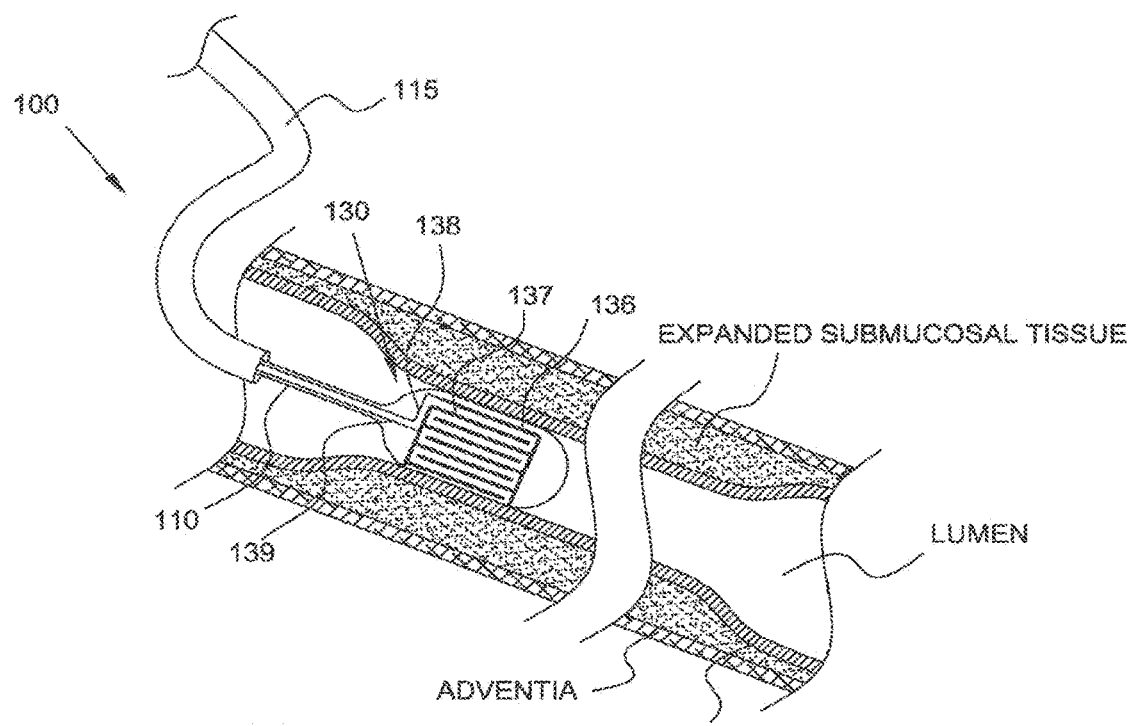
FIG. 2 is a side sectional view of the distal portion of an ablation device inserted into a duodenum, consistent with the present inventive concepts.
Figure 2A:
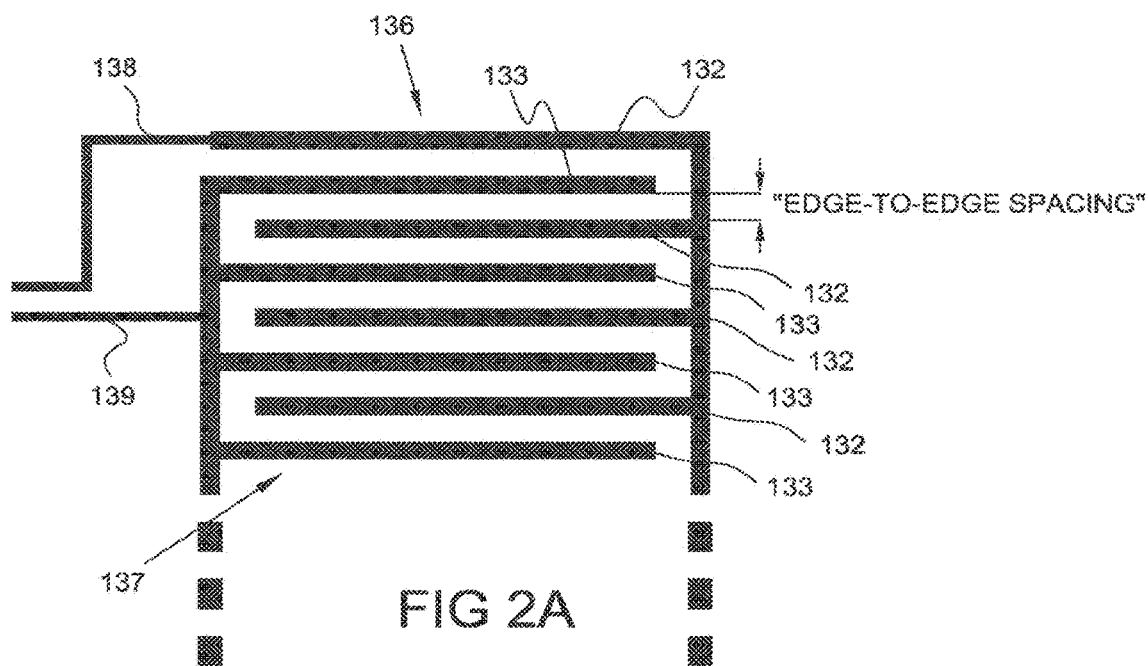
FIG. 2A is a magnified view of the distal portion of the ablation device of FIG. 2, consistent with the present inventive concepts.

Referring now to FIG. 2, a side sectional view of the distal portion of an ablation device inserted into a duodenum is illustrated, consistent with the present inventive concepts. Ablation device 100 comprises shaft 110, a relatively flexible, biocompatible, elongate structure configured for insertion into a body lumen, such as a lumen of the small intestine, such as the duodenal lumen shown. Shaft 110 is typically connected to a handle on its proximal end, not shown but configured to allow an operator to advance, retract and otherwise manipulate or control ablation device 100. Ablation device 100 can be constructed and arranged for delivery over a guidewire, via a lumen from a proximal portion to a distal portion, or via a rapid exchange sidecar in the distal portion of the device (lumen and sidecar not shown but well known to those of skill in the art). Expandable assembly 130 is mounted to a distal portion of shaft 110, and can comprise an inflatable balloon, cage or other expandable element as described in reference to FIG. 1 hereabove. Shaft 110 is shown inserted through introducer 115 which can comprise an endoscope, sheath, or other body introduction device. Expandable assembly 130 has been positioned in a portion of duodenal tissue that has had a segment of submucosal tissue expanded (e.g. a full circumferential segment of at least 50% of the duodenal submucosa expanded), such as has been described above. Expandable assembly 130 comprises two ablation elements, electrodes 136 and 137, each comprises multiple interdigitated elongate conductors as shown in FIG. 2 and described in detail in reference to FIG. 2A herebelow. Expandable assembly 130 has been radially expanded such as to contact the mucosal surface of the duodenum. Electrodes 136 and 137 are connected to wires 138 and 139, respectively, and constructed and arranged to be attached to an RF energy delivery source, such as EDU 330 of FIG. 1. Electrodes 136 and 137 can cover the full circumference (e.g. approximately 360°) of expandable assembly 130 or they can cover a partial circumference (e.g. an area covering between 45° and 300° of the outer surface of expandable assembly 130).

Referring additionally to FIG. 2A, a magnified view of electrodes 136 and 137 of FIG. 2 is illustrated, consistent with the present inventive concepts. Electrode 136 comprises multiple elongate conductors 132, each electrically connected to wire 138, and electrode 137 comprises multiple elongate conductors 133 each electrically connected to wire 139. Conductors 132 and 133 are typically in the interdigitated pattern shown such that RF energy can be delivered between the alternative pairs of relatively parallel conductors 132 of electrode 136 and conductors 133 of electrode 137. When expandable assembly 130 is expanded to contact tissue such as mucosal tissue, and RF energy is applied between electrodes 136 and 137, current passes from neighboring edges of conductors 132 and 133, through the contacted tissue, causing heating of the tissue. This heating, combined with conductive heating that occurs in neighboring tissue, ablates the tissue as has been described in reference to FIG. 1 hereabove. The spacing between the edges of the associated pairs of conductors 132 and 133 is termed herein "edge-to-edge" spacing and illustrated in FIG. 2A. Delivery of RF energy between the various pairs of conductors 132 and 133 is configured to cause at least ablation of the mucosa of the small intestine (e.g. duodenal mucosa). Ablation of at least a portion of the depth of the small intestine submucosa is typically caused by the RF energy delivered and resultant conductive heating. However, ablation of deeper layers, such as the adventitial layers (e.g. muscularis layers and/or serosal layers) is prevented or otherwise reduced to a near atraumatic level. After adequate energy delivery, expandable assembly 130 will be repositioned in a more distal segment of duodenum, with or without radially compacting assembly 130. Subsequently, a second energy delivery can be performed. The steps of repositioning and delivering energy are repeated until an adequate portion of small intestine is treated, typically greater than 50% of the length of the duodenal mucosa, or greater than 90% of the duodenal mucosa length. Alternatively or additionally, other tissue can be treated, such as has been described hereabove.

Conductors 132 and/or 133 comprise elongate structures whose major axis is positioned relatively parallel to the central axis of a body lumen when expandable assembly 130 is expanded within the body lumen. Conductors 132 and/or 133 and expandable assembly 130 can be constructed and arranged such that conductors 132 and/or 133 remain relatively parallel to the central axis of a body lumen when neighboring and/or within a curvilinear portion of that body lumen. Conductors 132 and/or 133 can be at least 10 mm long, such as at least 20 mm long. Conductors 132 and 133 can be arranged in the interdigitated pattern shown in FIG. 2A, such that bipolar RF energy passes between neighboring pairs of conductors. Conductors 132 and 133 can have an edge-to-edge spacing as described in reference to FIG. 1 hereabove. One or more pairs of conductors 132 and 133 can be arranged to remain relatively parallel when expandable assembly 130 is radially expanded. Electrodes 136 and/or 137 can include at least four conductors 132 and/or 133, respectively.

Referring now to FIG. 3, a side sectional view of the distal portion of an ablation device inserted into a curvilinear section of duodenum is illustrated, consistent with the present inventive concepts. Ablation device 100 comprises shaft 110, a relatively flexible, biocompatible, elongate structure configured for insertion into a body lumen, such as a lumen of the small intestine, such as the duodenal lumen shown. Shaft 110 is typically connected to a handle on its proximal end, not shown but configured to allow an operator to advance, retract and otherwise manipulate or control ablation device 100. Ablation device 100 can be constructed and arranged for delivery over a guidewire, via a lumen from a proximal portion to a distal portion, or via a rapid exchange sidecar in the distal portion of the device (lumen and sidecar not shown but well known to those of skill in the art). Expandable assembly 130 is mounted to a distal portion of shaft 110, and can comprise an inflatable balloon, cage or other expandable element as described in reference to FIG. 1 hereabove. Shaft 110 is shown inserted through introducer 115 which can comprise an endoscope, sheath, or other body introduction device. Expandable assembly 130 comprises an array of ablation elements, conductor array 135, such as an array of two or more electrodes which cover a full or partial circumferential portion of expandable assembly 130. In some embodiments, array 135 comprises multiple interdigitated elongate conductors between which bipolar RF energy is delivered, as has been described hereabove. Expandable assembly 130 has been positioned in a distal portion of duodenal tissue, such as a section that has had a segment of submucosal tissue expanded (expansion not shown but described in detail in reference to FIG. 2 hereabove). Relative tissue layer thicknesses and other relative dimensions shown in FIG. 3 are not to scale. Expandable assembly 130 has been radially expanded such as to contact the mucosal surface of the duodenum at a $1^{st}$ target tissue portion, which is distal to a series of target tissue portions comprising sequential target tissue portions 2 through 6 as shown in FIG. 3. Conductor array 135 is electrically connected to at least two wires, wires 138 and 139, which are constructed and arranged to be attached to an RF energy delivery source, such as EDU 330 of FIG. 1.

Expandable assembly 130 is sized to allow positioning in the curved segments of the gastrointestinal tract, such as a curved segment of the duodenum, such that expandable assembly 130 can be expanded to fully contact the mucosal wall without exerting undesired force onto tissue. In some embodiments, the length expandable assembly 130 is less than or equal to 30 mm, such as less than or equal to 25 mm, less than or equal to 20 mm or less than or equal to 15 mm. After application of RF energy (e.g. monopolar RF energy, bipolar RF energy and/or combined monopolar and bipolar RF energies), expandable assembly 130 will be repositioned to the $2^{nd}$ target tissue portion, just proximal to the $1^{st}$ target tissue portion, with or without contracting assembly 130 prior to the repositioning. Subsequently, second energy delivery can be performed. The steps of repositioning and delivering energy are repeated until target tissue portions 3, 4, 5 and 6 have been treated, typically greater than 50% of the length of the duodenal mucosa, or greater than 90% of the duodenal mucosal length. Alternatively or additionally, other tissue can be treated, such as has been described hereabove.

Target tissue portions 1 through 6 typically include common or overlapping tissue portions, such as is shown in FIG.

3. While the embodiment of FIG. 3 shows six target tissue portions being treated, more or less segments can be treated. Treatments (e.g. energy deliveries) are typically done in a contiguous manner (e.g. $1^{st}$ portion followed by $2^{nd}$ portion, followed by $3^{rd}$ portion, etc), however any order can be performed.

Figure 4:
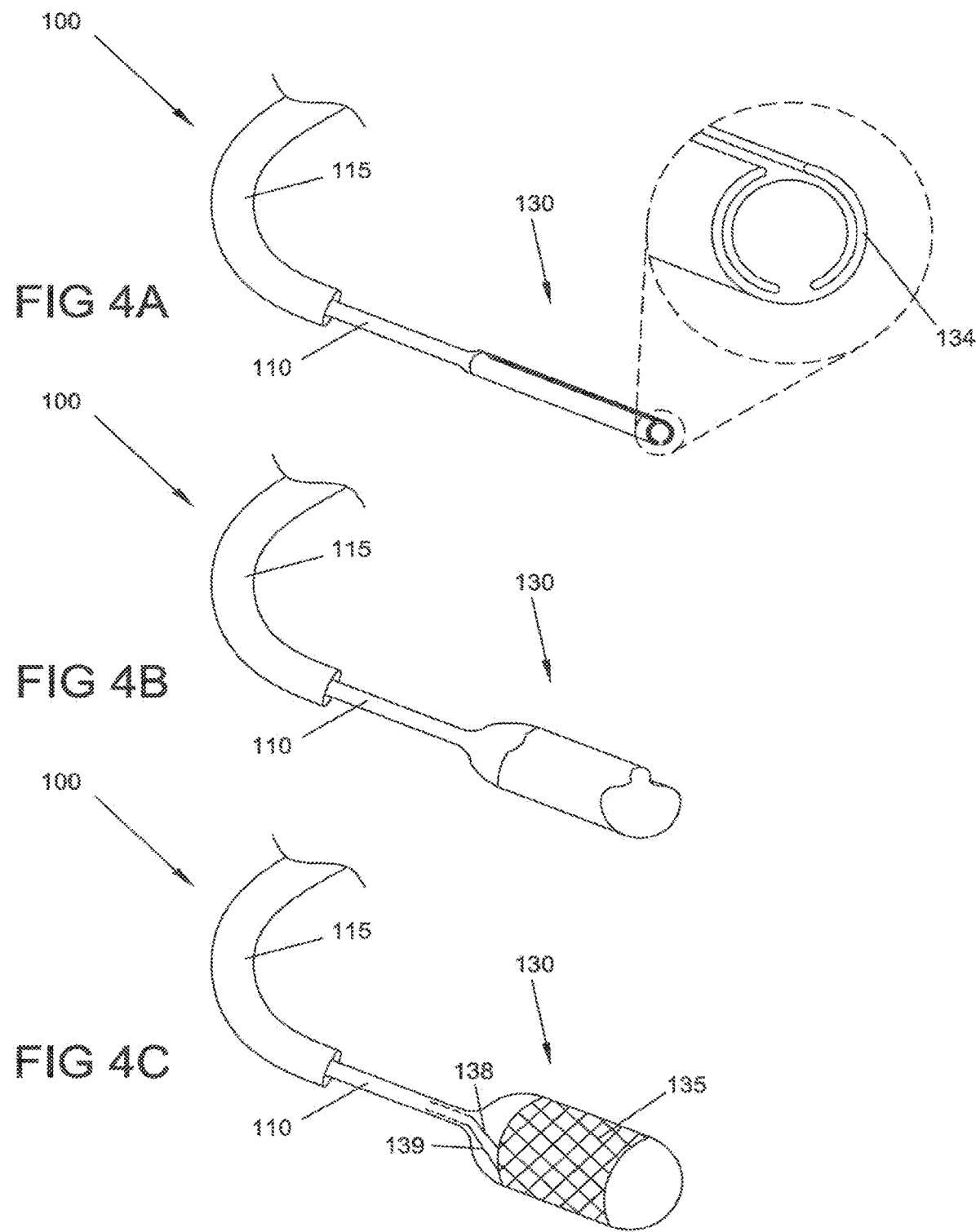
FIG. 4A is perspective and magnified end views of the distal portion of an ablation device comprising a foldable assembly, consistent with the present inventive concepts.
FIG. 4B is a perspective view of the ablation device of FIG. 4A, with the foldable assembly 130 in a partially expanded state (e.g. partially unfolded), consistent with the present inventive concepts.
FIG. 4C is a perspective view of the ablation device of FIG. 4A, with the foldable assembly in a fully expanded state, consistent with the present inventive concepts.

Referring now to FIG. 4A, perspective and magnified end views of the distal portion of an ablation device comprising a foldable assembly is illustrated, consistent with the present inventive concepts. Ablation device 100 comprises shaft 110, a relatively flexible, biocompatible, elongate structure configured for insertion into a body lumen, such as a lumen of the small intestine, such as a duodenal lumen. Shaft 110 is typically connected to a handle on its proximal end, not shown but configured to allow an operator to advance, retract and otherwise manipulate or control ablation device 100. Ablation device 100 can be constructed and arranged for delivery over a guidewire, via a lumen from a proximal portion to a distal portion, or via a rapid exchange sidecar in the distal portion of the device (lumen and sidecar not shown but well known to those of skill in the art). Expandable assembly 130 is mounted to a distal portion of shaft 110. Shaft 110 is shown inserted through introducer 115 which can comprise an endoscope, sheath, or other body introduction device. Expandable assembly 130 includes substrate 134, a sheet of material which is constructed and arranged to be folded and/or unfolded to radially compacted and expanded conditions, respectively. Substrate 134 can be flexible, and can include one or more heat set folds. Substrate 134 is shown in its radially compacted state in FIG. 4A. In FIG. 4B, a perspective view of the device of FIG. 4A is shown, with expandable assembly 130 in a partially expanded (e.g. partially unfolded). In FIG. 4C, a perspective view of the device of FIG. 4A is shown, with expandable assembly 130 in a fully expanded state. Substrate 134 comprises an array of conductors 135, which have been removed from FIGS. 4A and 4B for illustrative clarity. Substrate 134 can be configured to be folded and/or unfolded via one or more control mechanisms, not shown but such as the control rod described in reference to FIG. 10 herebelow. A control rod or other mechanism can be configured to be rotated and/or translated to fold and/or unfold substrate 134. Numerous mechanisms and/or configurations can be used to fold or unfold expandable assembly 130, such as a balloon attached to substrate 134 and positioned to unfold when the balloon is inflated or fold when the balloon is deflated (e.g. a negative pressure is applied to the balloon via one or more inflation tubes or lumens). In some embodiments, introducer 115 can be used to capture (e.g. cause to fold) substrate 134. In some embodiments, substrate 134 can be biased in a folded, partially folded, or fully unfolded states, such as via one or more heat sets used to create folds in a flexible material such as material selected from the group consisting of: polyamide; a polyester weave; a stretchable polyurethane material; and combinations of these.

Referring now specifically to FIG. 4C, expandable assembly 130 has been radially expanded such as to contact the mucosal surface of the small intestine (tissue not shown). Conductor array 135, now shown, can comprise one or more electrodes, such as one or more electrodes comprising an array of conductors, such as an array of two or more electrodes which cover a full or partial circumferential portion of expandable assembly 130. In some embodiments, array 135 comprises multiple interdigitated elongate conductors between which bipolar RF energy is delivered, as has been described hereabove in reference to FIG. 2A. Conductor array 135 is electrically connected to at least two wires, wires 138 and 139, which can be constructed and arranged to be attached to an RF energy delivery source, such as EDU 330 of FIG. 1.

Expandable assembly 130 can be sized to allow positioning in the curved segments of a gastrointestinal segment, such that expandable assembly 130 can be expanded to fully contact the mucosal wall without exerting undesired force onto tissue. In some embodiments, the length expandable assembly 130 is less than or equal to 30 mm, such as less than or equal to 25 mm, less than or equal to 20 mm or less than or equal to 15 mm. After application of RF energy (e.g. monopolar RF energy, bipolar RF energy and/or combined monopolar and bipolar RF energies), expandable assembly 130 can be repositioned for subsequent treatment of one or more additional target tissue portions, as has been described in reference to FIGS. 2 and 3 hereabove.

Figure 5:
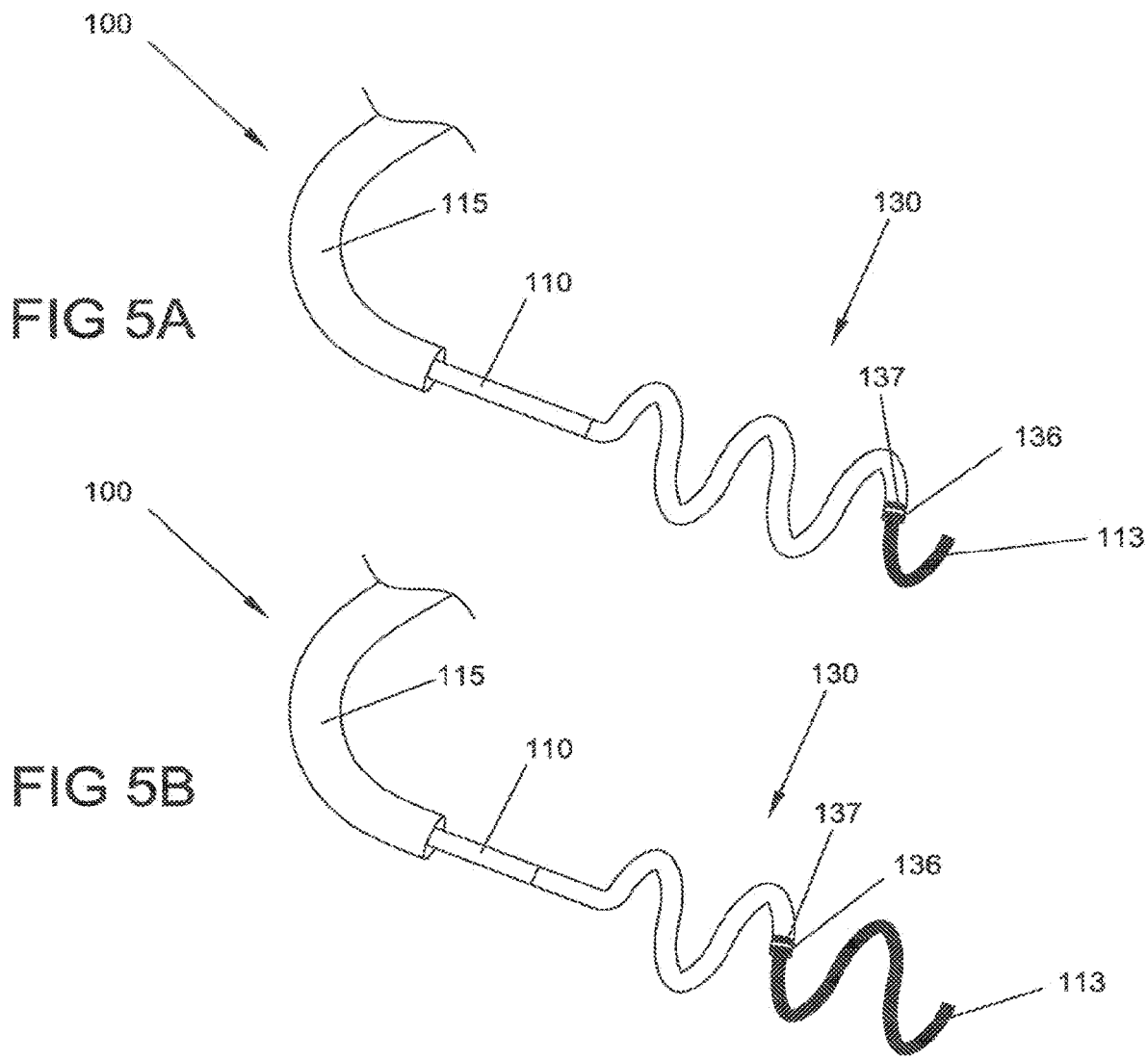
FIGS. 5A and 5B are side views of the distal portion of an ablation device comprising a helical coil, consistent with the present inventive concepts.

Referring now to FIGS. 5A and 5B, side views of the distal portion of an ablation device comprising a helical coil are illustrated, consistent with the present inventive concepts. Ablation device 100 comprises shaft 110, a relatively flexible, biocompatible, elongate structure configured for insertion into a body lumen such as a lumen of the small intestine. Shaft 110 is typically connected to a handle on its proximal end, not shown but configured to allow an operator to advance, retract and otherwise manipulate or control ablation device 100. Ablation device 100 can be constructed and arranged for delivery over a guidewire, via a lumen from a proximal portion to a distal portion, or via a rapid exchange sidecar in the distal portion of the device (lumen and sidecar not shown but well known to those of skill in the art). Continuous with shaft 110 is expandable assembly 130, a flexible tube mounted to the distal end of shaft 110, typically with a diameter approximating the diameter of the distal portion of shaft 110. Shaft 110 is shown inserted through introducer 115 which can comprise an endoscope, sheath, or other body introduction device. Expandable assembly 130 surrounds a curvilinear mandrel 113, typically a stainless steel, nickel titanium alloy or plastic filament which is biased in the helical configuration shown, and travels proximally within shaft 110 to its proximal end. Curvilinear mandrel 113 and expandable assembly 130 are constructed and arranged so that they can be radially compressed, such as to be captured within introducer 115.

Mounted to the distal end or a distal portion of shaft 110 are electrodes 136 and 137, such as two or more ring shaped electrodes surrounding a segment of expandable assembly 130. Electrodes 136 and 137 are each electrically attached to one or more wires, as has been described hereabove, traveling on, in or within shaft 110 to be attachable to an energy delivery unit, such as EDU 330 of FIG. 1. In some embodiments, three or more electrodes are included on expandable assembly 130. Expandable assembly 130 and curvilinear mandrel 113 are constructed and arranged such that the deployed helix circumferentially contacts gastrointestinal wall tissue, such as mucosal tissue of the duodenum or other small intestine location. Subsequently, electrodes 136 and 137 contact the tissue, such that RF energy can be delivered by or between electrodes 136 and 137 as has been described hereabove. In some embodiments, electrodes 136 and/or 137 can be covered by a dielectric material, and RF energy delivered to tissue through capacitive coupling, such as is described in reference to FIG. 10A herebelow.

In some embodiments, after sufficient energy has been delivered to a portion of target tissue, shaft 110 is retracted (e.g. via one or more controls on a proximal handle not shown), causing expandable assembly 130 to equally retract and electrodes 136 and 137 to be positioned proximate a different portion of target tissue. A subsequent energy delivery can be performed, and the repositioning and energy delivery steps repeated until a sufficient portion of gastrointestinal tissue is treated. In some embodiments, energy can be delivered as shaft 110 is retracted (e.g. as electrodes 136 and 137 move along a tissue surface), such as via a manual (e.g. operator driven) and/or automatic (e.g. via a motion transfer assembly such as motion transfer assembly 335 of FIG. 1) retraction. While the foregoing has been described in terms of retraction, advancement of shaft 110 can be performed to reposition electrodes 136 and 137, between and/or during energy deliveries.

Expandable assembly 130 and curvilinear mandrel 113 can be constructed and arranged to allow sufficient contact in curved segments of a gastrointestinal segment, such that expandable assembly 130 can be expanded to fully contact the mucosal wall without exerting undesired force onto tissue.

Figure 6:
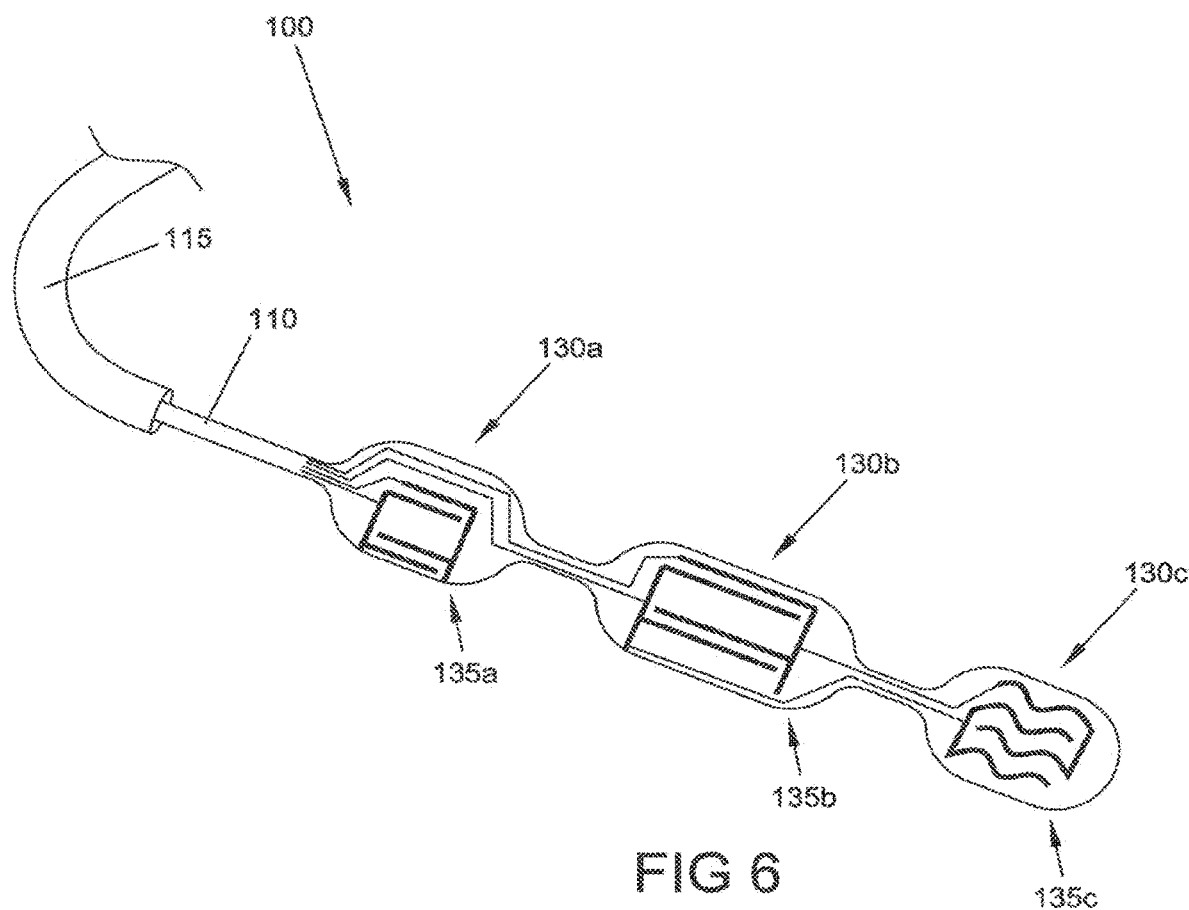
FIG. 6 is a side view of the distal portion of an ablation device including multiple expandable assemblies, consistent with the present inventive concepts.

Referring now to FIG. 6, a side view of the distal portion of an ablation device including multiple expandable assemblies is illustrated, consistent with the present inventive concepts. Ablation device 100 comprises shaft 110, a relatively flexible, biocompatible, elongate structure configured for insertion into a body lumen such as the lumen of the small intestine. Shaft 110 is typically connected to a handle on its proximal end, not shown but configured to allow an operator to advance, retract and otherwise manipulate or control ablation device 100. Ablation device 100 can be constructed and arranged for delivery over a guidewire, via a lumen from a proximal portion to a distal portion, or via a rapid exchange sidecar in the distal portion of the device (lumen and sidecar not shown but well known to those of skill in the art). Ablation device 100 comprises a first expandable assembly 130*a*, a more distal second expandable assembly 130*b*, and a further distal third expandable assembly 130*c*, each shown in their radially expanded condition. Expandable assemblies 130*a*, 130*b* and/or 130*c* each can comprise an inflatable balloon, cage or other expandable element as described in reference to FIG. 1 hereabove. Shaft 110 is shown inserted through introducer 115 which can comprise an endoscope, sheath, or other body introduction device. Expandable assemblies 130*a*, 130*b* and 130*c* each comprise an array of conductors, arrays 135*a*, 135*b* and 135*c*, respectively, each connected to one or more wires as shown, and constructed and arranged to receive electrical energy as has been described in detail hereabove. In some embodiments, ablation device 100 includes four or more expandable assemblies, such as four or more expandable assemblies each comprise an array of conductors.

Expandable assemblies 130*a*, 130*b* and/or 130*c* are sized to allow positioning in the curved segments of a gastrointestinal segment such as a curved segment of the small intestine (e.g. a curved segment of the duodenum), such that each expandable assembly 130*a*, 130*b* and 130*c* can be expanded to fully contact the mucosal wall without exerting undesired force onto tissue. In some embodiments, the length of expandable assemblies 130*a*, 130*b* and/or 130*c* is less than or equal to 30 mm, such as less than or equal to 25 mm, less than or equal to 20 mm, or less than or equal to 15 mm. In some embodiments, two or more of expandable assemblies 130*a*, 130*b* and/or 130*c* comprises a length of less than or equal to 20 mm. In some embodiments, expandable assemblies 130*a*, 130*b* and/or 130*c* comprise similar lengths and/or expanded diameters. In some embodiments, expandable assemblies 130*a*, 130*b* and/or 130*c* comprise different lengths and/or expanded diameters. Expandable assemblies 130*a*, 130*b* and/or 130*c* can be separated by similar or different separation distances. In some embodiments, expandable assemblies 130*a*, 130*b* and/or 130*c* are separated by a distance less than the length of the next assembly distal to it, such that untreated target tissue can be treated by retracting shaft 110 and performing a second ablation.

In some embodiments, conductor arrays 135*a*, 135*b* and 135*c* comprise similar configurations of conductors. In other embodiments, such as the embodiment of FIG. 6, conductor arrays 135*a*, 135*b* and 135*c* comprise different configurations of conductors. For example, conductor arrays 135*a* and 135*b* contain pairs of relatively linear conductors that are radially offset from each other. In this offset configuration, energy can be applied to conductor array 135*b* to treat a partial circumferential segment of gastrointestinal tissue while expandable assembly 130*b* is at a first axial location. Subsequently, shaft 110 can be advanced such that expandable assembly 130*a* moves distally to be positioned in the same first axial location. Delivery of energy to conductor array 135*a* will cause a different target tissue portion to be treated due to the offset in conductor patterns between array 135*b* and 135*a*. Each of the conductor arrays 135*a*, 135*b* and 135*c*, can comprise linear or curvilinear conductors, such as the curvilinear conductor pairs included in expandable assembly 130*c*.

After application of RF energy (e.g. monopolar RF energy, bipolar RF energy and/or combined monopolar and bipolar RF energies), shaft 110 can be advanced or retracted to position each of expandable assemblies 130*a*, 130*b* and 130*c* in new locations. Energy delivery can be performed during or after translation of shaft 110, and until a sufficient length of tissue has been treated, as has been described hereabove. In some embodiments, the target tissue comprises a set of sequential target tissue portions comprising, in order, a first section, a second section, a third section, a fourth section, and a fifth section, for example where the expandable assemblies 130*a*, 130*b* and 130*c* are positioned to ablate the first, third and fifth target tissue portions in a first energy delivery and expandable assemblies 130*a* and 130*b* are positioned to ablate the second and fourth target tissue portions in a second energy delivery.

Figure 7:
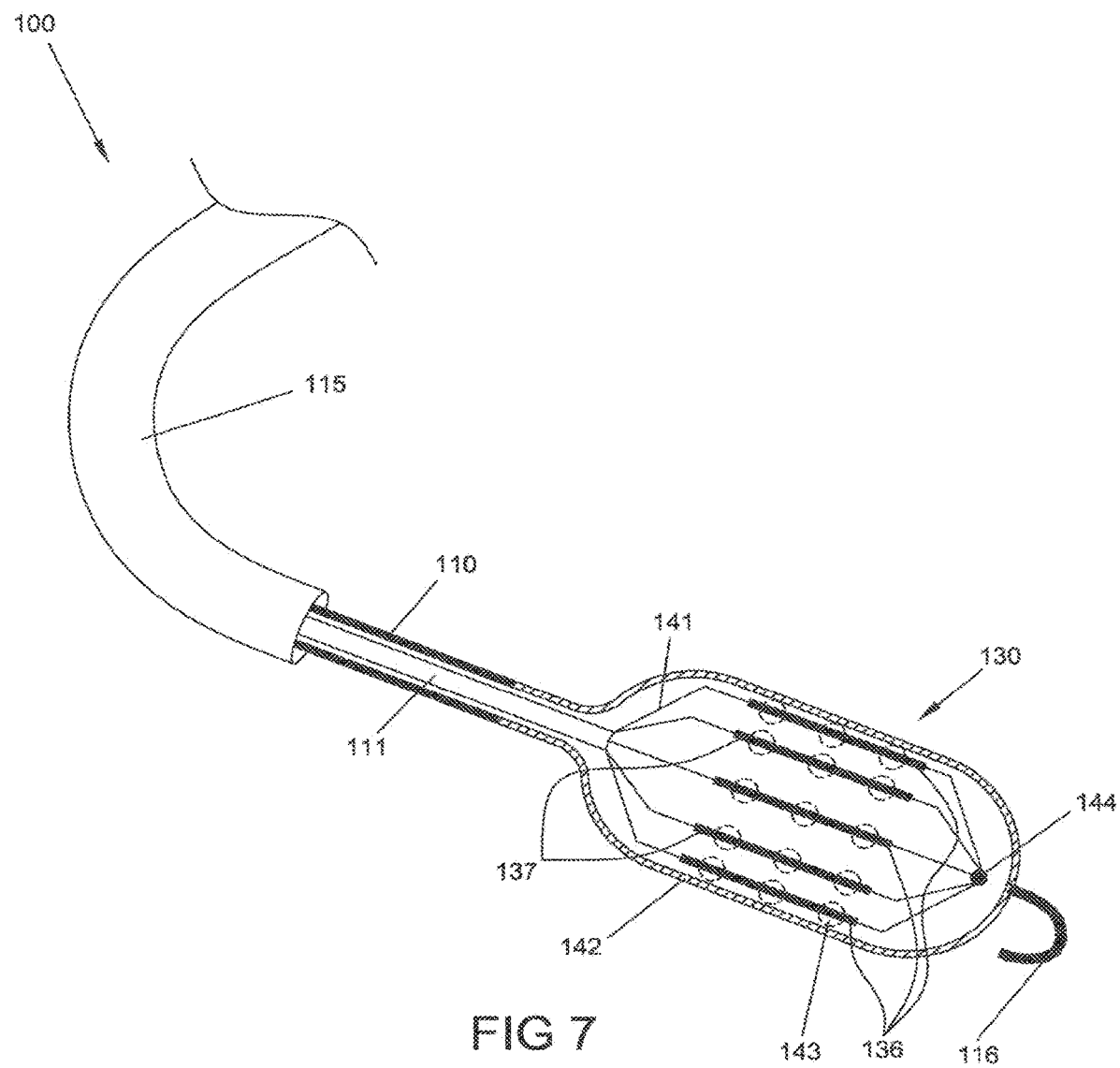
FIG. 7 is a side sectional view of a distal portion of an ablation device including an expandable assembly comprising a balloon surrounding an expandable scaffold, consistent with the present inventive concepts.

Referring now to FIG. 7, a side sectional view of a distal portion of an ablation device including an expandable assembly comprising a balloon surrounding an expandable scaffold is illustrated, consistent with the present inventive concepts. Ablation device 100 comprises shaft 110, a relatively flexible, biocompatible, elongate structure configured for insertion into a body lumen such as a lumen of the small intestine (e.g. into the duodenal lumen). Shaft 110 is typically connected to a handle on its proximal end, not shown but configured to allow an operator to advance, retract and otherwise manipulate or control ablation device 100. Ablation device 100 can be constructed and arranged for delivery over a guidewire, via a lumen from a proximal portion to a distal portion, or via a rapid exchange sidecar in the distal portion of the device (lumen and sidecar not shown but well known to those of skill in the art). Ablation device 100, and the other ablation devices of the present inventive concepts, can include a flexible guidewire tip, such as guidewire tip 116 shown in FIG. 7, configured to support atraumatic advancement of device 100 through a gastrointestinal lumen. Shaft 110 is shown inserted through introducer 115 which can comprise an endoscope, sheath, or other body introduction device.

Expandable assembly 130 is mounted to a distal portion of shaft 110, and includes an expandable inner cage comprising multiple splines 141 which are attached at their distal ends to hub 144 and at their proximal ends to the distal end of inner shaft 111. Expandable assembly 130 further includes balloon 142 surrounding splines 141. Balloon 142 includes multiple openings 143 as shown. Openings 143 are positioned to coincide with electrodes 136 and 137, each comprising the multiple elongate conductors shown, mounted to alternating splines 141. In some embodiments, electrodes 136 and/or electrodes 137 comprise a width greater than a diameter of openings 130. In some embodiments, electrodes 136 and/or electrodes 137 comprise a length greater that a diameter of openings 130. Balloon 142 and openings 143 are constructed and arranged such that tissue contacts electrodes 136 and 137 at the predetermined, fixed locations of openings 143, when expandable assembly 130 is positioned in gastrointestinal tissue in its radially expanded state. Openings 143 can comprise one or more different shaped openings, such as openings with a perimeter comprising a geometry selected from the group consisting of; a circle; an oval; and a rectangle.

Splines 141 can be resiliently biased in a radially expanded condition, such as stainless steel or nickel titanium alloy splines biased in the bowed condition shown. Alternatively, one or more control rods can be included to control expansion, not shown but described in detail in reference to FIG. 10 herebelow. Expandable assembly 130 and splines 141 can be captured such as via retraction of shaft 110 to cause capture within introducer 115, and/or retraction of shaft 111 to cause capture within shaft 110. Electrodes 136 and 137 can comprise a circumferential array of conductors that cover the full circumference (e.g. approximately 360°) of expandable assembly 130 or the array can cover a partial circumference (e.g. an area covering between 45° and 300° of the outer surface of expandable assembly 130). In some embodiments, balloon 142 does not include openings 143, and monopolar and/or bipolar RF energy can be delivered to tissue via capacitive coupling through balloon 142 functioning as a dielectric between electrodes 136 and/or 137 and the target tissue. In some embodiments, one or more electrodes can be positioned on the outer surface of balloon 142, such as one or more electrodes constructed and arranged to deliver monopolar and/or bipolar RF energy to target tissue.

Electrodes 136 and 137 are connected to one or more wires, not shown but configured to deliver monopolar and/or bipolar RF energy to electrodes 136 and 137, and treat at least a portion of target tissue as described hereabove. After adequate energy delivery, expandable assembly 130 can be repositioned in a different segment of gastrointestinal tissue, with or without radially compacting assembly 130. Subsequently, a second energy delivery can be performed. The steps of repositioning and delivering energy are repeated until the desired complete segment of target tissue is treated. In some embodiments, the target tissue comprises greater than 50% of the length of the duodenal mucosa, or greater than 90% of the duodenal mucosa length. Alternatively or additionally, other tissue can be treated, such as has been described hereabove.

Figure 8A:
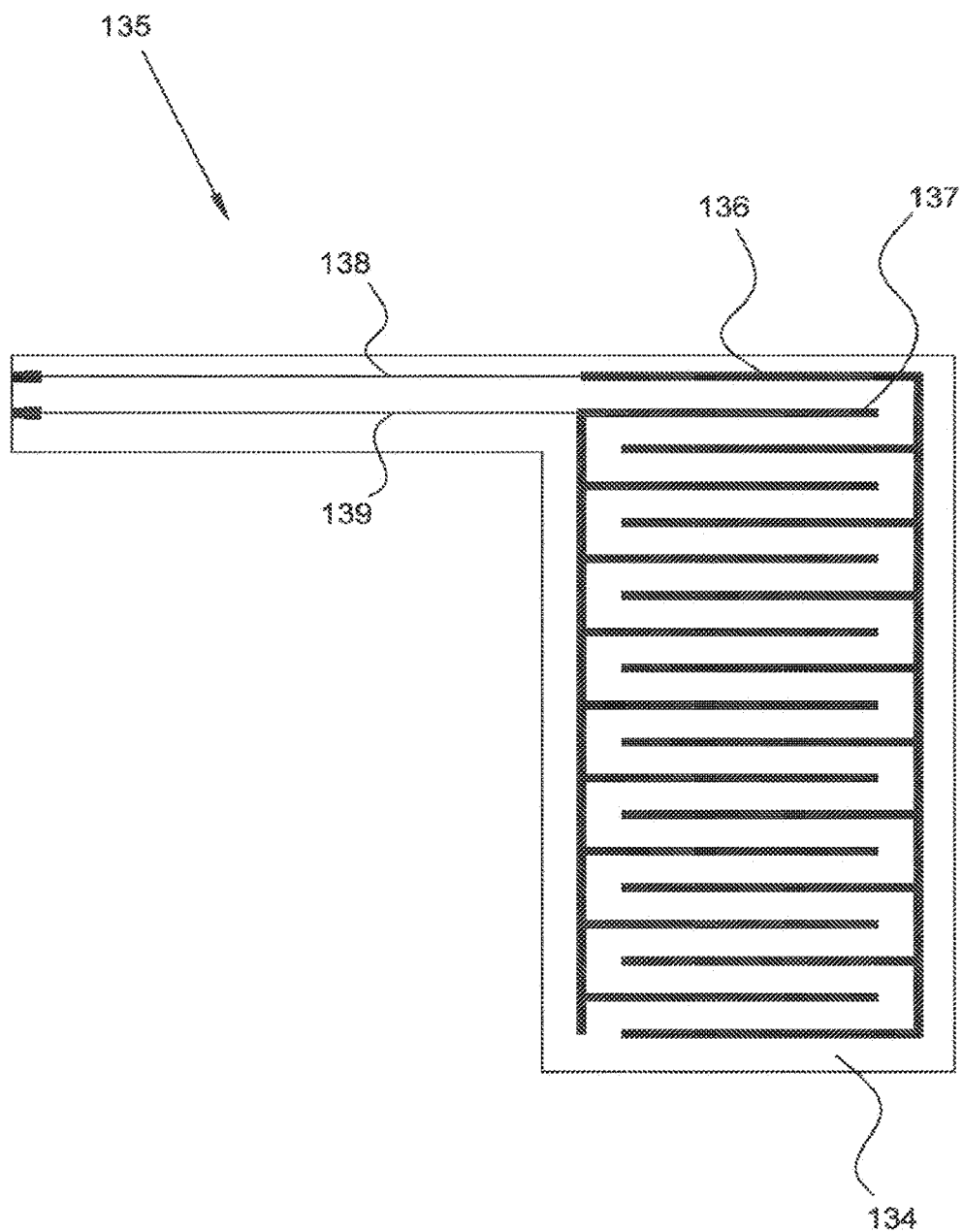
FIG. 8A is a side view of a conductor array including two electrodes each comprising multiple elongate conductors, consistent with the present inventive concepts.

Referring now to FIG. 8A, a side view of a conductor array including two electrodes each comprising multiple elongate conductors is illustrated, consistent with the present inventive concepts. Conductor array 135 comprises substrate 134 onto which electrodes 136 and 137 are attached. Electrodes 136 and 137 comprise multiple elongate conductors in the interdigitated, parallel pattern shown in FIG. 8A. Electrodes 136 and/or 137 can be attached to substrate 134 in various ways, such as with an adhesive bond or mechanical connection such as a weld or swage. In some embodiments, electrodes 136 and/or 137 are deposited onto substrate 134, such as via an ink-jet deposition such as an ink-jet deposition in which catalytic ink is deposited and then exposed to a copper solution. In some embodiments, electrodes 136 and/or 137 are deposited onto substrate 134 using a masked deposition process.

Electrodes 136 and 137 are attached on their proximal ends to wires 138 and 139, respectively, such as to be attached to wires of an ablation device as has been described hereabove. In some embodiments, substrate 134 comprises material selected from the group consisting of: polyamide; a polyester weave; a stretchable polyurethane material; and combinations of these. Substrate 134 can be biased in the flat configuration shown in FIG. 8A, or it can include a resilient bias, such as a bias into a tube shape. Electrodes 136 and 137 comprise an array of conductors covering substantially the entire surface area of substrate 134, such that when substrate 134 is transitioned to a tubular configuration, electrodes 136 and 137 can deliver RF energy to substantially a full circumferential portion of tubular tissue, such as a segment of small intestine mucosal tissue (e.g. duodenal mucosal tissue).

Substrate 134 can be to be positioned on the distal end or on a distal portion of a shaft, such as shaft 110 described in reference to numerous figures hereabove, and configured to radially expand to contact luminal wall tissue and/or radially compact to be captured by the shaft of an ablation device. Alternatively, substrate 134 can be mounted to an expandable element, such as a balloon; an expandable cage; a stent-like structure; an array of splines; and combinations of these. In these embodiments, substrate 134 comprises a flexibility sufficient to accommodate the expansion and/or contraction of the expandable element to which it is mounted. In alternative embodiments, three or more electrodes are included on substrate 134.

Figure 8B:
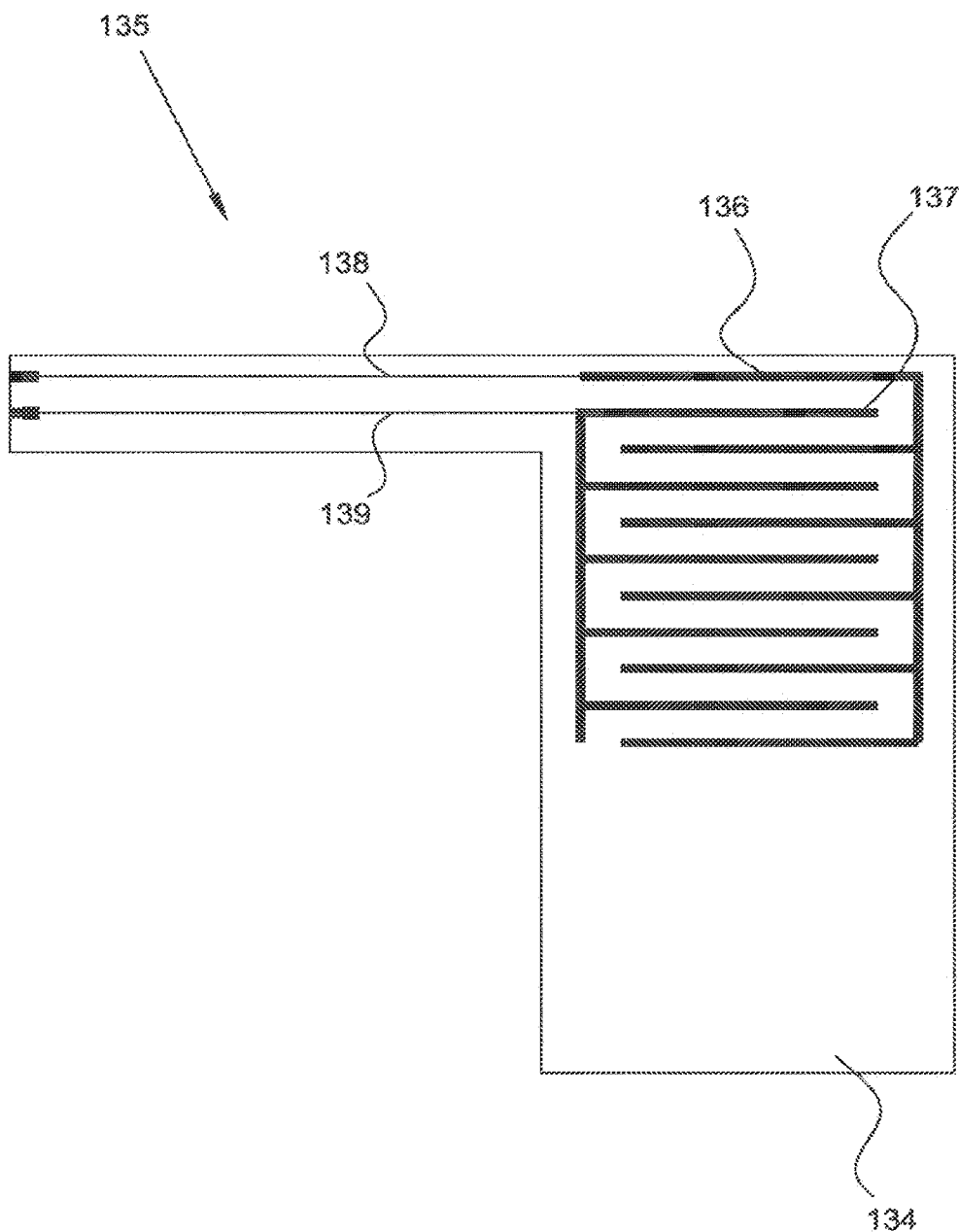
FIG. 8B is a side view of a conductor array including two electrodes each comprising multiple elongate conductors, consistent with the present inventive concepts.

Referring now to FIG. 8B, a side view of a conductor array including two electrodes each comprising multiple elongate conductors is illustrated, consistent with the present inventive concepts. Conductor array 135 is of similar construction and arrangement as conductor array 135 of FIG. 8A, with the exception that the conductors of electrodes 136 and 137 cover less than substantially the full surface area of substrate 134. In this configuration, a full circumferential ablation is typically performed by a first energy delivery, a rotation of array 135, and at least a subsequent second energy delivery. Electrodes 136 and 137 are attached on their proximal ends to wires 138 and 139, respectively, as shown. Wires 138 and 139 can be attached to one or more conductors of an ablation catheter, such as to deliver energy to electrodes 136 and 137, respectively, as has been described hereabove.

Figure 8C:
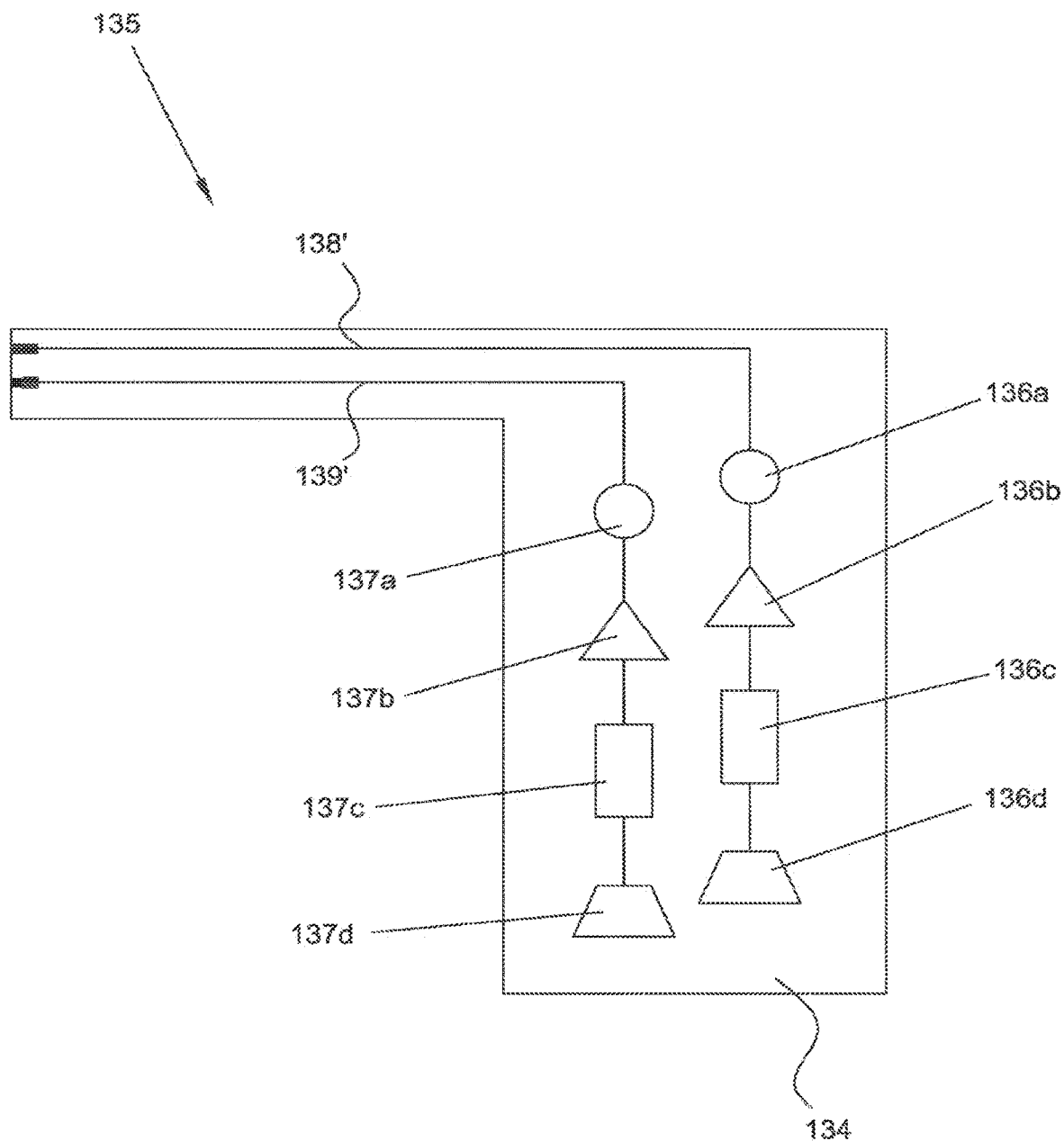
FIG. 8C is a side view of a conductor array including two electrodes each comprising multiple elongate conductors, consistent with the present inventive concepts.

Referring now to FIG. 8C, a side view of a conductor array including two electrodes each comprising multiple elongate conductors is illustrated, consistent with the present inventive concepts. Conductor array 135 comprises substrate 134 onto which multiple electrodes are mounted. Substrate 134 can be of similar materials, construction and arrangement, and it can be attached to a shaft, deployed in a lumen, and/or deliver energy as described in reference to substrate 134 of FIG. 8A.

Conductor array 135 of FIG. 8C comprises multiple, varying shape electrodes such as round shaped electrodes 136a and 137a, triangle shaped electrodes 136b and 137b, rectangle shaped electrodes 136c and 137c, and trapezoid shaped electrodes 136d and 137d. Conductor array 135 can comprise various shapes and orientations of electrodes, pairs of electrodes, conductors and/or pairs of conductors, such as those shown in FIG. 8C or otherwise. Conductors of conductor array 135 can comprise a shape selected from the group consisting of: rectangle; square; triangle; trapezoid; and combinations of these. Alternatively or additionally, electrodes 136*a-d* and/or 137*a-d* can be constructed and arranged to treat a target tissue portion with a shape selected from the group consisting of: rectangle; square; triangle; trapezoid; and combinations of these. Electrodes 136*a-d* and electrodes 137*a-d* are connected to wire bundles 138' and 139', respectively. Wire bundles 138' and 139' can comprise a single conductor, such that each group of electrodes are electrically connected, or it bundles 138' and 139' can comprise multiple, independent conductors, such that that each electrode can be electrically isolated.

Referring now to FIG. 8D, side and end views of an expandable assembly including a helical array of conductors are illustrated, consistent with the present inventive concepts. Expandable assembly 130 comprises substrate 134, configured in the tubular construction shown. Expandable assembly 130 can be attached to the distal end or distal portion of a shaft, such as has been described above. Expandable assembly can comprise an expandable element configured to radially expand and/or contract, not shown but typically a balloon, expandable cage or other expandable element as has been described hereabove.

Expandable assembly 130 includes electrodes 136 and 137, each comprising the alternating helical geometry shown in FIG. 8D, each helix fixedly mounted to substrate 134 as has been described hereabove. Electrodes 136 and 137 are electrically attached to wires 138 and 139, respectively, such that monopolar and/or bipolar RF energy can be applied to or between electrodes 136 and 137 as has been described hereabove.

Substrate 134 of FIGS. 8A-C can be attached to one or more expandable assemblies, such as an array of three or more expandable splines, such that substrate 134 and electrodes 136 and 137 mounted thereon, can be expanded such as to contact target tissue. Referring now to FIG. 8E, expandable assembly 130' comprises substrate 134 attached to three splines 141. Splines 141 are constructed and arranged to expand as shown, such that substrate 134 and mounted electrodes 136 and 137 comprise a relatively triangular cross sectional geometry. Target tissue, such as tubular target tissue such as a segment of small intestine tissue, can be distended or otherwise manipulated to electrically contact electrodes 136 and 137 while substrate 134 is expanded to this relatively triangular cross sectional geometry. Referring now to FIG. 8F, expandable assembly 130" comprises substrate 134 attached to four splines 141. Splines 141 are constructed and arranged to expand as shown, such that substrate 134 and mounted electrodes 136 and 137 comprise a relatively square cross sectional geometry. Target tissue, such as tubular target tissue such as a segment of small intestine tissue, can be distended or otherwise manipulated to electrically contact electrodes 136 and 137 while substrate 134 is expanded to this relatively square cross sectional geometry. Referring now to FIG. 8G, expandable assembly 130''' comprises substrate 134 attached to five splines 141. Splines 141 are constructed and arranged to expand as shown, such that substrate 134 and mounted electrodes 136 and 137 comprise a relatively pentagonal cross sectional geometry. Target tissue, such as tubular target tissue such as a segment of small intestine tissue, can be distended or otherwise manipulated to electrically contact electrodes 136 and 137 while substrate 134 is expanded to this relatively pentagonal cross sectional geometry. It should be appreciated that six or more splines 141 can be included, such as to expand substrate 134 to a hexagonal or other non-circular geometry. Electrodes 136 and 137 of FIGS. 8E-8G can be connected to one or more electrical wires, not shown but traveling proximally for attachment to a source of electrical energy as has been described hereabove.

Referring now to FIGS. 9A, 9B and 9C, distal portions of three ablation devices with three different tissue contacting portions are illustrated, consistent with the present inventive concepts. Ablation devices 100*a*, 100*b* and 100*c* of FIGS. 9A, 9B and 9C, respectively, are each shown exiting an introducer 115, as has been described hereabove. Ablation devices 100*a-c* each include shaft 110. Each shaft 110 can include a steering assembly comprising a pull wire 146 attached at its distal end to anchor 147, and at its proximal end to a control on a handle, control and handle not shown but configured to steer the distal portion of shaft 110 by translating pull wire 146. Ablation device 100*a* of FIG. 9A includes a round array of conductors 135*a*. Ablation device 100*b* of FIG. 9B includes a triangle shaped array of conductors 135*b*. Ablation device 100*c* of FIG. 9C includes a rectangle shaped array of conductors 135*c*. In other embodiments, various other shapes can be employed for an array of conductors, such as one or more shapes used to treat a similarly shaped target tissue portion, or a target tissue portion that can be treated by sequentially delivering electrical energy to tissue through arrays of these one or more shapes. Typical shapes include but are not limited to: triangle; rectangle; pentagon; hexagon; trapezoid; and combinations of these. Conductor arrays 135*a-c* are connected to one or more wires, not shown but traveling proximally through shaft 110 such as to be attached to an energy delivery unit (e.g. EDU 330 of FIG. 1) such that bipolar and/or monopolar RF energy can be delivered to target tissue.

Referring now to FIG. 10, the distal portion of an ablation device comprising multiple spline-mounted electrodes is illustrated, consistent with the present inventive concepts. Ablation device 100 comprises shaft 110, a relatively flexible, biocompatible, elongate structure configured for insertion into a body lumen such as a lumen of the small intestine. Shaft 110 is typically connected to a handle on its proximal end, not shown but configured to allow an operator to advance, retract and otherwise manipulate or control ablation device 100. Ablation device 100 can be constructed and arranged for delivery over a guidewire, via a lumen from a proximal portion to a distal portion, or via a rapid exchange sidecar in the distal portion of the device (lumen and sidecar not shown but well known to those of skill in the art). Shaft 110 is shown inserted through introducer 115 which can comprise an endoscope, sheath, or other body introduction device.

Expandable assembly 130 is mounted to a distal portion of shaft 110, and includes an expandable cage comprising multiple splines 141 which are attached at their distal ends to hub 144 and at their proximal ends to the distal end of shaft 110. Splines 141 can be resiliently biased in a radially expanded condition, such as stainless steel or nickel titanium alloy splines biased in the bowed condition shown. Alternatively, one or more control rods, such as control rod 145, can be used to operably expand and/or contract expandable assembly 130, such as when splines 141 are biased in a linear configuration. Control rod 145 is attached at its distal end to hub 144, and at its proximal end to a control of a handle on the proximal end of shaft 110. Advancement of control rod 145 (e.g. via a knob, lever or other control on the handle) causes expandable assembly 130 to radially collapse or compact, and retraction of control rod 145 causes expandable assembly 130 to radially expand.

Each spline 141 comprises one or more electrodes, such as electrodes 136 and 137 as shown. Each electrode is connected to one or more wires, not shown but configured to deliver monopolar and/or bipolar RF energy to electrodes 136 and 137, such as to treat at least a portion of target tissue when expandable assembly 130 has been expanded to contact target tissue. After expansion of expandable assembly 130, and performance of a first energy delivery to target tissue, expandable assembly 130 can be repositioned in a different segment of gastrointestinal tissue, with or without radially compacting assembly 130. Subsequently, a second energy delivery can be performed. The steps of repositioning and delivering energy are repeated until the desired segment of target tissue is treated in its entirety. In some embodiments, the target tissue comprises greater than 50% of the length of the duodenal mucosa, or greater than 90% of the duodenal mucosa length. Alternatively or additionally, other tissue can be treated, such as has been described hereabove.

In some embodiments, electrodes 136 and/or 137 are covered with a dielectric material, covering 148 as shown in the sectional side view of a spline 141 illustrated in FIG. 10A. Covering 148 comprises a dielectric material such as polytetrafluoroethylene, and is configured to cause capacitive coupling of electrodes 136 and/or 137 to target tissue. In some embodiments, electrodes 136 and/or 137 comprise a disk shaped electrode and covering 148 comprises a disk-shaped cover with thicker end portions (versus a thinner middle portion), such that the capacitively coupled RF energy delivered to tissue avoids edge effects (e.g. current concentration along the edge of an electrode 136 and/or 137) and results in uniform depth of tissue ablation.

Figure 10B:
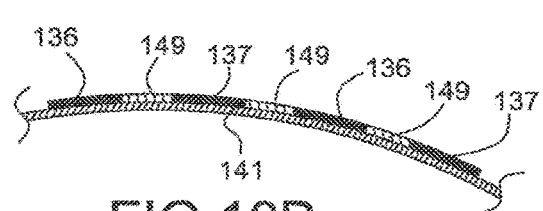
FIG. 10B is a side sectional view of an array of electrodes separated by thermal conductors, consistent with the present inventive concepts.

In some embodiments, one or more electrodes 136 and/or 137 are separated by a thermally conductive, electrically insulating spacer 149, as shown in the sectional side view of a spline 141 illustrated in FIG. 10B. Spacers 149 are positioned between two or more electrodes 136 and/or 137 and can comprise a thermally conductive, electrically insulating material selected from the group consisting of: sapphire; fused quartz; fused silica; a polymeric material; glass; and combinations of these.

Figure 10C:
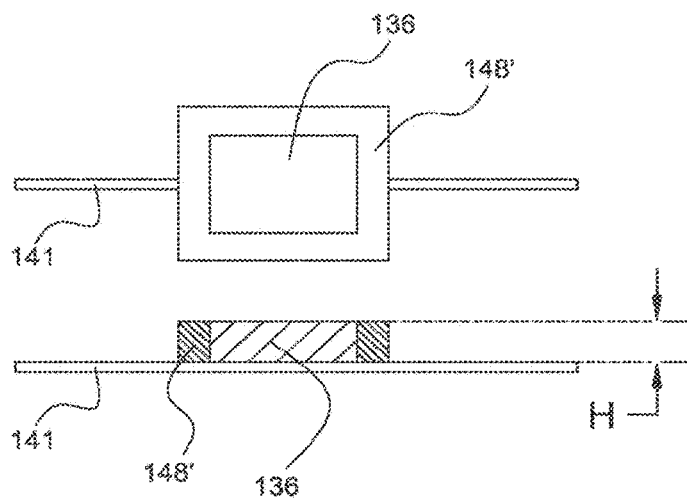
FIG. 10C is a top and side sectional view of an electrode with a top surface offset from a spline, consistent with the present inventive concepts.

Referring now to FIG. 10C, top and side sectional views of an electrode with a top surface offset from a spline are illustrated, consistent with the present inventive concepts. Electrode 136 comprises a bottom surface mounted to spline 141 (e.g. via a weld or swage attachment) and a top surface positioned at a distance from spline 141, electrode 136 height H as shown. In some embodiments, height H is at least 100 microns, such that the top surface of electrode 136 can extend into tissue with an irregular surface such as into villi of the small intestine (e.g. into villi of the duodenum). In some embodiments, height H is at least 200 microns, or at least 400 microns. Electrode 136 height H can be chosen to maximize or otherwise improve the amount of electrical energy delivered into tissue.

The sides of electrode 136 (e.g. surfaces relatively orthogonal to or otherwise continuous with the top surface of electrode 136) can be surrounded by an insulating material, such as insulator 148' as shown. Insulator 148' can cover some or all of the bottom surface of electrode 136. Insulator 148' can be constructed and arranged such that only the top surface of electrode 136 is conductive (e.g. to minimize current delivered from electrode 136 side and/or bottom surfaces). Insulator 148' can comprise a low-conductivity material, such as polytetrafluoroethylene, or an electrically insulating coating.

Spline 141 can comprise multiple electrodes 136 with heights similar to height H such that bipolar RF energy can be delivered between two or more of the electrodes. Alternatively or additionally, an ablation device of the present inventive concepts can comprise multiple splines 141 each with at least one electrode 136, such that bipolar RF energy can be delivered between two or more of the splines.

Figure 11:
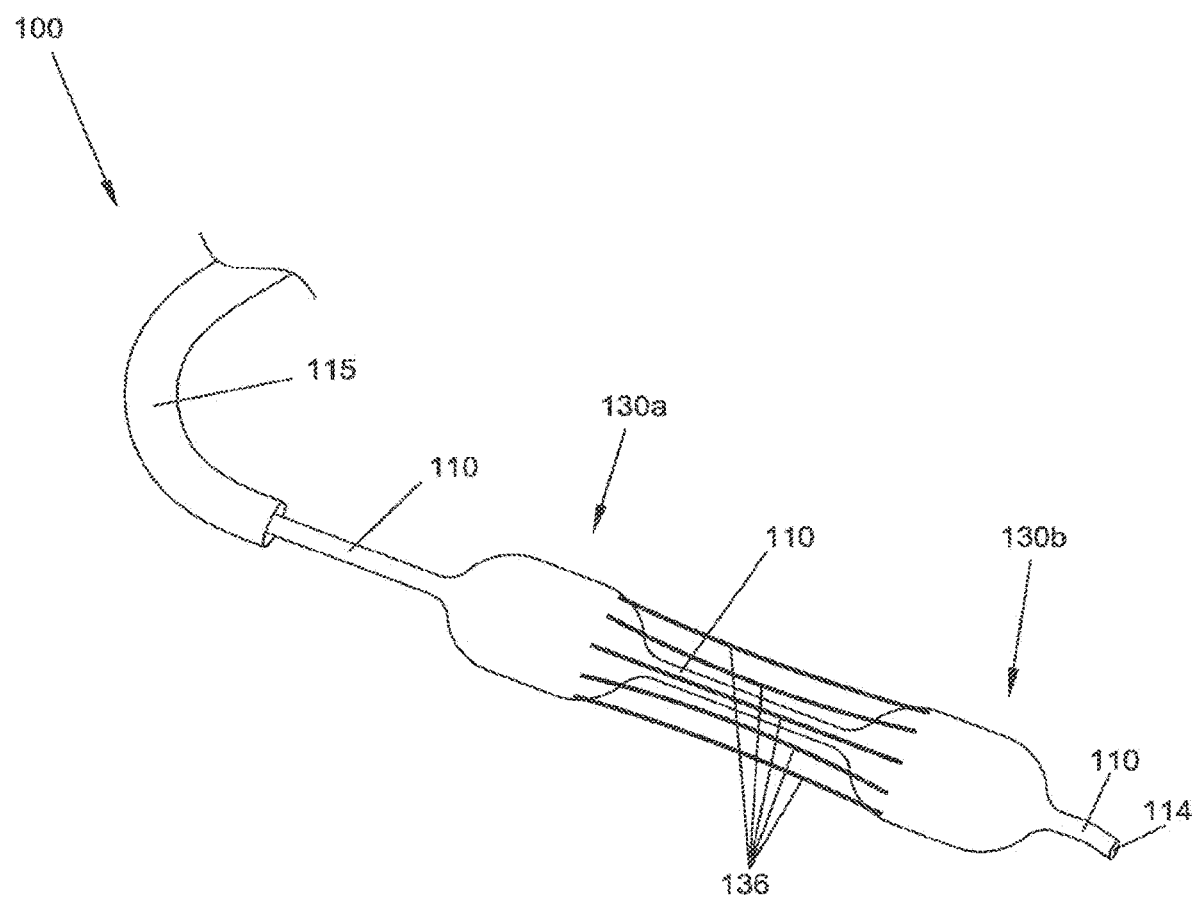
FIG. 11 is a distal portion of an ablation device including two expandable elements and intervening conductive filaments, consistent with the present inventive concepts.

Referring now to FIG. 11, a distal portion of an ablation device including two expandable elements and intervening conductive filaments is illustrated, consistent with the present inventive concepts. Ablation device 100 comprises shaft 110, a relatively flexible, biocompatible, elongate structure configured for insertion into a body lumen such as a lumen of the small intestine (e.g. the lumen of the duodenum). Shaft 110 is typically connected to a handle on its proximal end, not shown but configured to allow an operator to advance, retract and otherwise manipulate or control ablation device 100. Ablation device 100 can be constructed and arranged for delivery over a guidewire, via a lumen from a proximal portion to a distal portion, or via a rapid exchange sidecar in the distal portion of the device (lumen and sidecar not shown but well known to those of skill in the art). Two expandable assemblies, expandable assemblies 130a and 130b, are mounted to a distal portion of shaft 110 as shown. Expandable assemblies 130a and 130b can comprise an inflatable balloon, cage or other expandable element as described in reference to FIG. 1 hereabove. Shaft 110 is shown inserted through introducer 115 which can comprise an endoscope, sheath, or other body introduction device. Expandable assembly 130b has been positioned in a portion of duodenal tissue that has had a segment of submucosal tissue expanded (e.g. a full circumferential segment of at least 50% of the duodenal submucosa expanded), such as has been described above.

Positioned between expandable assembly 130a and 130b is a circumferential array of conductors, electrodes 136. Expandable assemblies 130a and 130b and electrodes 136 are positioned and arranged such that when expandable assemblies 130a and 130b are radially expanded to contact gastrointestinal wall tissue (e.g. mucosal tissue), electrodes 136 contact tissue. Electrodes 136 are attached to one or more wires, not shown but configured to allow delivery of monopolar and/or bipolar by or between and one or more electrodes 136, as has been described hereabove. In some alternative embodiments, one or more electrodes 136 are positioned on one or more filaments extending between expandable assemblies 130a and 130b.

Ablation device 100, or any of the ablation devices of the present inventive concepts, can be constructed to accommodate over-the-wire delivery, such as by the inclusion of lumen 114 which exits the distal end of shaft 110 and travels proximally, such as to a guidewire introduction port, not shown but typically attached to a proximal handle as has been described hereabove.

Figure 12:
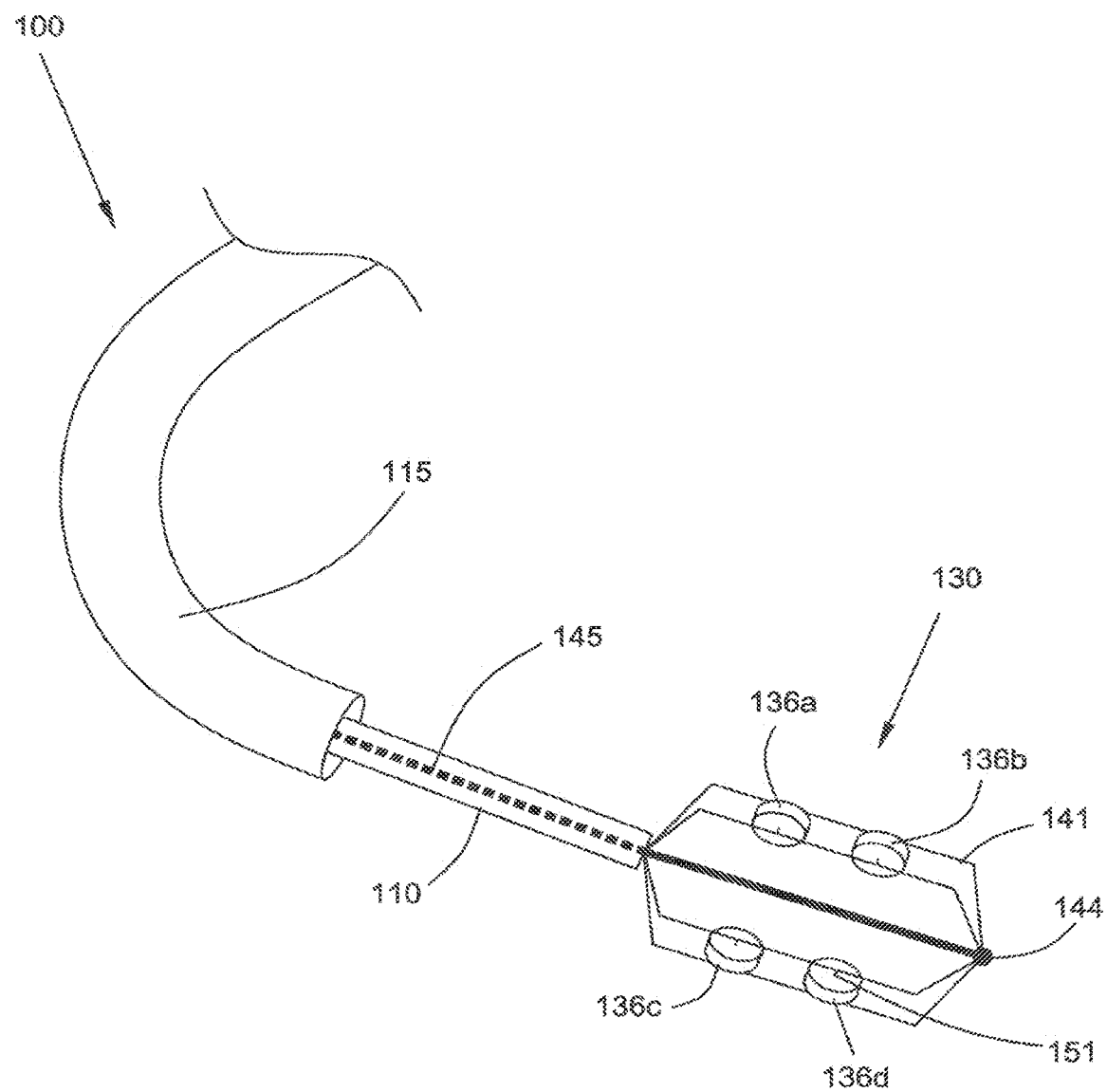
FIG. 12 is a distal portion of an ablation device including rotatable electrodes, consistent with the present inventive concepts.

Referring now to FIG. 12, a distal portion of an ablation device including rotatable electrodes is illustrated, consistent with the present inventive concepts. Ablation device 100 comprises shaft 110, a relatively flexible, biocompatible, elongate structure configured for insertion into a body lumen such as a lumen of the small intestine (e.g. the lumen of the duodenum). Shaft 110 is typically connected to a handle on its proximal end, not shown but configured to allow an operator to advance, retract and otherwise manipulate or control ablation device 100. Ablation device 100 can be constructed and arranged for delivery over a guidewire, via a lumen from a proximal portion to a distal portion, or via a rapid exchange sidecar in the distal portion of the device (lumen and sidecar not shown but well known to those of skill in the art). Shaft 110 is shown inserted through introducer 115 which can comprise an endoscope, sheath, or other body introduction device.

Expandable assembly 130 is mounted to a distal portion of shaft 110, and includes an expandable cage comprising multiple splines 141 which are attached at their distal ends to hub 144 and at their proximal ends to the distal end of shaft 110. Splines 141 can be resiliently biased in a radially expanded condition, such as stainless steel or nickel titanium alloy splines biased in the bowed condition shown. Alternatively, one or more control rods, such as control rod 145, can be used to operably expand and/or contract expandable assembly 130, such as when splines 141 are biased in a linear configuration. Control rod 145 is attached at its distal end to hub 144, and at its proximal end to a control of a handle on the proximal end of shaft 110. Advancement of control rod 145 (e.g. via a knob, lever or other control on the handle) causes expandable assembly 130 to radially collapse or compact, and retraction of control rod 145 causes expandable assembly 130 to radially expand. In an alternative embodiment, control rod 145 is attached to the proximal end of splines 141, such that advancement of control rod 145 causes expandable assembly 130 to radially expand, and retraction of control rod 145 causes expandable assembly 130 to radially compact. As stated above, radial compression of expandable assembly 130 can be used to stop or reduce delivery of energy to tissue.

Attached to splines 141 are multiple electrodes 136a-d. Electrodes 136a-d can be rotatably attached to splines 141 via axels 151 as shown. Electrodes 136a-d are electrically attached to one or more wires, not shown but as described hereabove. Electrodes 136a-d can be attached to the one or more wires via axels 151, such as a frictionally engaging electrical connection that allows electrical energy to be transferred through each axel 151 to the associated electrode 136a-d as the electrode 136a-d is rotating. In some embodiments, electrodes 136a-d are each electrically attached to individual wires such that monopolar and/or bipolar energy can be delivered any of electrodes 136a-d or between any electrodes 136a-d. When expandable assembly 130 is expanded such that electrodes 136a-d contact tissue (e.g. luminal wall tissue), electrodes 136a-d are constructed and arranged such that they rotate along a tissue surface as shaft 110 and/or introducer 115 is advanced or retracted.

A sufficient quantity of electrodes 136a-d (e.g. one or more on each spline 141), such as to cover a full circumferential (e.g. approximately 360°) axial segment of expandable assembly 130. Alternatively, electrodes 136a-d can cover a partial circumference (e.g. an area covering between 45° and 300°) of the outer surface of an axial segment of expandable assembly 130.

A first energy delivery can be delivered to electrodes 136a-d, such as to treat target tissue or a portion of target tissue. Subsequently, expandable assembly 130 can be translated axially or distally, and one or more subsequent energy deliveries performed. In some embodiments, RF energy is delivered as the electrodes 136a-d rotate along a tissue surface. The steps of translating and/or repositioning, and delivering energy are repeated until the desired segment of target tissue is treated in its entirety. In some embodiments, the target tissue comprises greater than 50% of the length of the duodenal mucosa, or greater than 90% of the duodenal mucosa length. Alternatively or additionally, other tissue can be treated, such as has been described hereabove.

The foregoing description and accompanying drawings set forth a number of examples of representative embodiments at the present time. Various modifications, additions and alternative designs will become apparent to those skilled in the art in light of the foregoing teachings without departing from the spirit hereof, or exceeding the scope hereof, which is indicated by the following claims rather than by the foregoing description. All changes and variations that fall within the meaning and range of equivalency of the claims are to be embraced within their scope.

What is claimed is:

1. A method of ablating mucosal tissue in a patient's duodenum, the method comprising:
   introducing an ablation device into the patient's gastrointestinal (GI) tract;
   advancing the ablation device to a first location in the patient's duodenum, the ablation device comprising an elongate shaft with a radially expandable element attached to the elongate shaft, the radially expandable element being moveable between contracted states and expanded states, the ablation device being introduced and advanced to the patient's duodenum with the radially expandable element in a contracted state;
   ablating mucosal tissue at the first location in the patient's duodenum by:
      moving the radially expandable element to an expanded state such that an array of conductors mounted to the radially expandable element forms a substantially tubular shape that directly contacts mucosal tissue of the duodenum of the first location; and
      causing a first delivery of electrical energy to the array of conductors;
   after the first delivery of electrical energy, moving the radially expandable element to a contracted state and then moving the ablation device to a second location in the patient's duodenum; and
   ablating mucosal tissue at the second location in the patient's duodenum by:
      moving the radially expandable element to an expanded state such that the array of conductors forms a substantially tubular shape that directly contacts mucosal tissue of the duodenum of the second location; and
      causing a second delivery of electrical energy to the array of conductors;
   wherein the first and second locations are distal to the patient's ampulla of Vater, and
   wherein the method comprises ablating a majority of the patient's duodenal mucosal tissue distal to the patient's ampulla of Vater by ablating additional locations with electrical energy from the array of conductors after the first and second locations.

2. The method of claim 1, wherein the electrical energy comprises a pulsed waveform configured to ablate contacted mucosal tissue by generating a pulsed and/or modulated electric field.

3. The method of claim 1, wherein the array of conductors comprises at least two conductors each comprising a height of at least 100 microns.

4. The method of claim 1, further comprising, before a delivery of electrical energy, causing a vacuum to apply a suction force to mucosal tissue contacted by the array of conductors.

5. The method of claim 1, wherein a total axial length the patient's duodenum ablated with electrical energy comprises at least 50% of a length of the patient's duodenum distal to the patient's ampulla of Vater.

6. The method of claim 1, wherein the radially expandable element comprises a balloon.

7. The method of claim 1, wherein electrical energy is delivered for a time period of at least 5 seconds.

8. The method of claim 1, wherein the ablating comprises a non-desiccating ablation of the target tissue.

9. The method of claim 1, wherein the expandable element is configured to, in an expanded state, direct contact with a majority of a circumferential ring of tissue around the expandable element.

10. The method of claim 1, wherein the ablating is configured to cause apoptosis and/or cell necrosis of the target tissue.

11. The method of claim 1, wherein moving the radially expandable element to the expanded state comprises causing a motion control mechanism of the ablation device to move the radially expandable element.

12. The method of claim 11, wherein the motion control mechanism comprises a rotational drive assembly configured to advance the radially expandable element to the expanded state and retract the radially expandable element to the contracted state.

13. The method of claim 1, wherein the first location and the second location are adjacent and/or partially overlapping.

14. The method of claim 1, wherein at least a portion of the radially expandable element is biased towards a tubular shape in the expanded state.

15. The method of claim 1, wherein the radially expandable element comprises a radially expandable sheet.

16. The method of claim 15, wherein moving the radially expandable element between the expanded state and the contracted state comprises furling or unfurling the radially expandable sheet.

17. The method of claim 1, wherein the radially expandable element is resiliently biased in the expanded state.

18. A method of ablating mucosal tissue in a patient's duodenum, the method comprising:
   introducing an ablation device into the patient's gastrointestinal (GI) tract;
   advancing the ablation device to a first location in the patient's duodenum, the ablation device comprising an elongate shaft with a radially expandable element attached to the elongate shaft, the radially expandable element being moveable between a contracted state and an expanded state, the ablation device being introduced and advanced to the patient's duodenum in the contracted state;
   at the first location in the patient's duodenum:
      moving the radially expandable element to the expanded state such the radially expandable element forms a substantially cylindrical shape that directly contacts mucosal tissue of the duodenum of the first location; and
      causing a first delivery of energy to the mucosal tissue of the first location via the radially expandable element;
   after the first delivery of energy, moving the radially expandable element to the contracted state and then moving the ablation device to a second location in the patient's duodenum;
   at the second location in the patient's duodenum:
      moving the radially expandable element to the expanded state such that radially expandable element forms a substantially cylindrical shape that directly contacts mucosal tissue of the duodenum of the second location; and
      causing a second delivery of energy to the mucosal tissue of the second location via the radially expandable element;
   wherein the first and second locations are distal to the patient's ampulla of Vater;
   wherein the method comprises treating a majority of the patient's duodenal mucosal tissue distal to the patient's ampulla of Vater by treating additional locations after the first and second locations with energy from the radially expandable element.

19. The method of claim 18, wherein the expandable element comprises a balloon.

20. The method of claim 18, wherein the first and second deliveries of energy comprise delivery of a heated fluid to the expandable element.

21. The method of claim 18, wherein the first and second deliveries of energy comprise delivery of a cryogenic fluid to the expandable element.

22. The method of claim 18, wherein the first location and the second location are adjacent or partially overlapping.

23. A method of ablating mucosal tissue in a patient's duodenum, the method comprising:
   introducing an ablation device into the patient's gastrointestinal (GI) tract;
   advancing the ablation device to a starting location in the patient's duodenum that is distal to the patient's ampulla of Vater, the ablation device comprising an elongate shaft with a radially expandable element attached to the elongate shaft, the radially expandable element being moveable between contracted states and expanded states, the ablation device being introduced and advanced to the patient's duodenum with the radially expandable element in a contracted state;
   ablating mucosal tissue at a plurality of locations in the patient's duodenum by:
      (a) moving the radially expandable element to an expanded state such that an array of conductors mounted to the radially expandable element forms a substantially tubular shape that directly contacts mucosal tissue of the duodenum of a respective location of the plurality of locations; and
      (b) causing a delivery of electrical energy to the array of conductors;
      (c) after the delivery of electrical energy, moving the radially expandable element to a contracted state and then moving the ablation device to a different location of the plurality of locations; and
      (d) repeating (a), (b) and (c) to ablate a majority of the patient's duodenal mucosal tissue distal to the patient's ampulla of Vater.

24. The method of claim 23, wherein the different location of the plurality of locations is adjacent to and/or partially overlapping with the respective location.

25. The method of claim 23, wherein the electrical energy comprises a pulsed waveform configured to ablate contacted mucosal tissue by generating a pulsed and/or modulated electric field.

26. The method of claim 23, wherein the ablating is configured to cause apoptosis and/or cell necrosis of the target tissue.

27. The method of claim 23, wherein the radially expandable element comprises a radially expandable sheet.

28. The method of claim 27, wherein moving the radially expandable element between the expanded state and the contracted state comprises furling or unfurling the radially expandable sheet.

29. The method of claim 23, further comprising, before a delivery of electrical energy, causing a vacuum to apply a suction force to mucosal tissue contacted by the array of conductors.

* * * * *